United States Patent [19]
Allgeier

[11] Patent Number: 5,633,379
[45] Date of Patent: May 27, 1997

[54] 3-HETEROALIPHATYL- AND 3-HETERO (ARYL)ALIPHATYL-2(1H)-QUINOLONE DERIVATIVES

[75] Inventor: Hans Allgeier, Lörrach, Germany

[73] Assignee: Ciba-Geigy Corporation, Tarrytown, N.Y.

[21] Appl. No.: 456,358

[22] Filed: Jun. 1, 1995

[30] Foreign Application Priority Data

Jun. 2, 1994 [CH] Switzerland ............... 1732/94

[51] Int. Cl.$^6$ ............... A61K 31/47; C07D 215/227; C07D 215/20; C07D 215/36
[52] U.S. Cl. ............... 546/155
[58] Field of Search ............... 546/155; 514/312

[56] References Cited

FOREIGN PATENT DOCUMENTS

| | | |
|---|---|---|
| 0459561 | 12/1991 | European Pat. Off. . |
| 0489458 | 6/1992 | European Pat. Off. . |
| 9306829 | 4/1993 | WIPO . |
| 9310783 | 6/1993 | WIPO . |
| 9311115 | 6/1993 | WIPO . |

OTHER PUBLICATIONS

Leeson, Paul "Glycine–Site N–Methyl–D–Aspartate Receptor Antagonists" Drug Design for Neuroscience: 339–361 (1993).
McQuaid et al., "3–Phenyl–4–Hydroxyquinolin–2(1H)–ones": Patent and Selective Antagonists at the.
Carling, Robert et al. "3–Nitro–3, 4–Dihydro–2(1H)–Quinolones Excitatory Amino Acid Antagonists Acting".
"At Glycine–Site NMDA and (RS)–α–Amino–3–Hydroxy–5–Methyl–4–Isoxazolepropionic Acid receptors" J. Med. Chem. 36: 3397–3408 (1993).
Rowley, Michael et al "3–Acyl–4–Hydroxyquinolin–2(1H)–ones". Systemically Active Anticonvolsants Acting by Antagonism at the Glycine Site of the N–Methyl–D–Aspartate Receptor Complex J. Med. Chem. 36: 3386–3396 (1993).
Leeson, Paul D. et al. "Amino Acid Bioisosteres: Design of 2–Quinolone Derivatives as Glycine–Site N–Methyl–D–Aspartate Receptor Antagonists" Bioorganic & Medicinal Chemistry Letters, 3(2): 299–304 (1993).

*Primary Examiner*—C. Warren Ivy
*Assistant Examiner*—D. Margaret M. Mach
*Attorney, Agent, or Firm*—Marla J. Mathias; Ronald J. Campbell; Karen G. Kaiser

[57] ABSTRACT

3-Heteroaliphatyl- and 3-hetero(aryl)aliphatyl-2(1H) quinolone derivatives of formula I wherein the radicals $R_1$, $R_2$, $R_3$ and $R_4$ are each independently of the others hydrogen, an aliphatic hydrocarbon radical, free or etherified hydroxy, mercapto or etherified and/or oxidised mercapto, unsubstituted or aliphaticaliy substituted amino, nitro, free or esterified or amidated carboxy, cyano, free or amidated sulfamoyl, halogen or trifluoromethyl, X is oxy or optionally oxidised thio, A is a divalent aliphatic radical and $R_5$ is an optionally partially hydrogenated aryl or heteroaryl radical that is unsubstituted or substituted by aliphatic or araliphatic hydrocarbon radicals, by free or etherified hydroxy, by mercapto or etherified and/or oxidised mercapto, by unsubstituted or aliphatically substituted amino, by aliphatic acyl, by free or esterified or amidated carboxy, by cyano, by free or amidated sulfamoyl, by halogen and/or by trifluoromethyl; free or etherified hydroxymethyl; cyano; or free or esterified or amidated carboxy, and tautomers and/or salts thereof, have antagonistic properties with respect to excitatory amino acids and can be used for the treatment of pathological conditions that are responsive to glycine-antagonistic blocking of NMDA-sensitive receptors.

6 Claims, No Drawings

3-HETEROALIPHATYL- AND 3-HETERO (ARYL)ALIPHATYL-2(1H)-QUINOLONE DERIVATIVES

The invention relates to novel 3-heteroaliphatyl- and 3-hetero(aryl)aliphatyl-2(1H)-quinolone derivatives of formula I

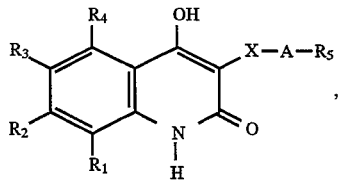

wherein the radicals $R_1$, $R_2$, $R_3$ and $R_4$ are each independently of the others hydrogen, an aliphatic hydrocarbon radical, free or etherified hydroxy, mercapto or etherified and/or oxidised mercapto, unsubstituted or aliphatically substituted amino, nitro, free or esterified or amidated carboxy, cyano, free or amidated sulfamoyl, halogen or trifluoromethyl, X is oxy or optionally oxidised thio, A is a divalent aliphatic radical and $R_5$ is an optionally partially hydrogenated aryl or heteroaryl radical that is unsubstituted or substituted by aliphatic or araliphatic hydrocarbon radicals, by free or etherified hydroxy, by mercapto or etherified and/or oxidised mercapto, by unsubstituted or aliphatically substituted amino, by aliphatic acyl, by free or esterified or amidated carboxy, by cyano, by free or amidated sulfamoyl, by halogen and/or by trifluoromethyl; free or etherified hydroxymethyl; cyano; or free or esterified or amidated carboxy, and to the tautomers and/or salts thereof, to pharmaceutical compositions comprising the novel compounds, and to the use thereof as medicinal active ingredients.

Aliphatic hydrocarbon radicals are, for example, lower alkyl or lower alkenyl radicals, but may also be lower alkynyl radicals.

Optionally partially hydrogenated aryl radicals are, for example, monocyclic aryl radicals, such as phenyl, bicyclic aryl radicals, such as naphthyl or indenyl, or partially hydrogenated bicyclic aryl radicals that are preferably bonded via a saturated carbon atom, such as 1,2,3,4-tetrahydronaphth-1-yl, 1,2,3,4-tetrahydronaphth-2-yl, indan-1-yl or indan-2-yl. The said aromatic radicals may contain one or more of the mentioned substituents, which may be identical or different, that is to say they may be mono-, di- or tri-substituted.

Optionally partially hydrogenated heteroaryl radicals are, for example, monocyclic or bicyclic heteroaryl radicals that are bonded via a carbon atom and contain as hetero atom(s) 1,2, 3 or 4 nitrogen atoms or 1 oxygen or sulfur atom, such as pyrrolyl, indolyl, furyl, benzfuranyl, thienyl, benzthienyl, imidazolyl, benzimidazolyl, oxazolyl, benzoxazolyl, thiazolyl, benzthiazolyl, tetrazolyl, pyridyl, quinolinyl, isoquinolinyl, pyrimidinyl, quinazolinyl, pyridazinyl, cinnolinyl, pyrazinyl, quinoxalinyl or triazinyl, or partially hydrogenated bicyclic heteroaryl radicals that are preferably bonded via a saturated carbon atom and contain 1 or 2 oxygen or sulfur atoms, such as chroman-3-yl, chroman-4-yl or 1,4-benzdioxan-2-yl. The said aromatic radicals may contain one or more of the mentioned substituents, which may be identical or different, that is to say they may be mono-, di- or tri-substituted.

Free or etherified hydroxy is, for example, hydroxy or lower alkoxy, but may also be lower alkenyloxy or lower alkynyloxy.

Free or etherified hydroxymethyl is, for example, hydroxymethyl or phenyloxymethyl.

Mercapto or etherified and/or oxidised mercapto is, for example, optionally oxidised mercapto or lower alkylthio, such as mercapto, sulfo, lower alkylthio, lower alkanesulfinyl or lower alkanesulfonyl, but may also be optionally oxidised lower alkenylthio or lower alkynyl-thio, such as lower alkenesulfonyl.

Aliphatically substituted amino is, for example, N-mono- or N,N-di-lower alkylamino.

Free or esterified or amidated carboxy is, for example, carboxy, lower alkoxycarbonyl; phenyl-lower alkoxycarbonyl that is unsubstituted or substituted by lower alkyl, lower alkoxy, hydroxy, halogen and/or by trifluoromethyl; carbamoyl, N-mono- or N,N-di-lower alkyl-carbamoyl, or N-phenylcarbamoyl or N-phenyl-N-lower alkyl-carbamoyl each of which is unsubstituted or substituted in the phenyl moiety by lower alkyl, lower alkoxy, hydroxy, halogen and/or by trifluoromethyl.

Free or amidated sulfamoyl is, for example, sulfamoyl or N-mono- or N,N-di-lower alkyl-sulfamoyl.

Optionally oxidised thio is thio, sulfinyl or sulfonyl.

The divalent aliphatic radical A is, for example, a lower alkylene radical substituted by free or esterified carboxy, such as carboxy or lower alkoxycarbonyl, or, in a position higher than the α-position to the thio group, by free or etherified hydroxy, such as hydroxy, lower alkoxy or secondly lower alkenyloxy or lower alkynyloxy. Such radicals that may be given special mention are: lower alkylene, carboxy-lower alkylene, lower alkoxycarbonyl-lower alkylene, and hydroxy-lower alkylene, lower alkoxy-lower alkylene, lower alkenyloxy-lower alkylene and lower alkynyloxy-lower alkylene carrying the hydroxy, lower alkoxy, lower alkenyloxy or lower alkynyloxy group in a position higher than the α-position.

Aliphatic acyl is, for example, lower alkanoyl.

Hereinabove and hereinbelow, lower radicals and compounds are to be understood, for example, as being those containing up to and including 7, preferably up to and including 4, carbon atoms (C atoms).

Lower alkyl is, for example, $C_1$–$C_7$alkyl, preferably $C_1$–$C_4$alkyl, such as especially methyl or secondly ethyl, propyl, isopropyl or butyl, but may also be isobutyl, sec-butyl, tert-butyl or a $C_5$–$C_7$alkyl group, such as a pentyl, hexyl or heptyl group.

Lower alkenyl is, for example, $C_3$–$C_4$alkenyl, such as allyl or methallyl.

Lower alkynyl is, for example, $C_3$–$C_4$alkynyl, such as propargyl.

Lower alkoxy is, for example, $C_1$–$C_7$alkoxy, preferably $C_1$–$C_4$alkoxy, such as methoxy, ethoxy, propyloxy, isopropyloxy or butyloxy, but may also be isobutyloxy, sec-butyloxy, tert-butyloxy or a pentyloxy, hexyloxy or heptyloxy group.

Lower alkenyloxy is, for example, $C_3$–$C_4$alkenyloxy, such as allyloxy or methallyloxy.

Lower alkynyloxy is, for example, $C_3$–$C_4$alkynyloxy, such as propargyloxy.

Lower alkylthio is, for example, $C_1$–$C_7$alkylthio, preferably $C_1$–$C_4$alkylthio, such as methylthio, ethylthio, propylthio, isopropylthio or butylthio, but may also be isobutylthio, sec-butylthio, tert-butylthio or a pentylthio, hexylthio or heptylthio group.

Lower alkanesulfinyl is, for example, $C_1$–$C_7$alkanesulfinyl, preferably $C_1$–$C_4$alkanesulfinyl, such as methanesulfinyl, ethanesulfinyl, propanesulfinyl or butanesulfinyl, but may also be a pentanesulfinyl, hexanesulfinyl or heptanesulfinyl group.

Lower alkanesulfonyl is, for example, $C_1$–$C_7$alkanesulfonyl, preferably $C_1$–$C_4$alkanesulfonyl, such as methanesulfonyl, ethanesulfonyl, propanesulfonyl or butanesulfonyl, but may also be a pentanesulfonyl, hexanesulfonyl or heptanesulfonyl group.

Lower alkenylthio is, for example, $C_3$–$C_4$alkenylthio, such as allylthio or methallylthio.

Lower alkenesulfinyl is, for example, $C_3$–$C_4$alkenesulfinyl, such as prop-2-enesulfinyl or but-2-enesulfinyl.

Lower alkenesulfonyl is, for example, $C_3$–$C_4$alkenesulfonyl, such as prop-2-enesulfonyl or but-2-enesulfonyl.

Lower alkynylthio is, for example, $C_3$–$C_4$alkynylthio, such as propargylthio.

N-mono- or N,N-di-lower alkylamino is, for example, N-mono- or N,N-di-$C_1$–$C_7$alkylamino, preferably N-mono- or N,N-di-$C_1$–$C_4$alkylamino, such as especially methylamino, dimethylamino or secondly ethylamino, dimethylamino, propylamino, dipropylamino, isopropylamino, diisopropylamino, butylamino or dibutylamino, but may also be isobutylamino, sec-butylamino, tert-butylamino or a $C_5$–$C_7$alkylamino group, such as a pentylamino, hexylamino or heptylamino group.

Lower alkoxycarbonyl is, for example, $C_1$–$C_7$alkoxycarbonyl, preferably $C_1$–$C_4$alkoxycarbonyl, such as methoxycarbonyl, ethoxycarbonyl, propyloxycarbonyl, isopropyloxycarbonyl or butyloxycarbonyl, but may also be isobutyloxycarbonyl, sec-butyloxycarbonyl, tert-butyloxy-carbonyl or a pentyloxycarbonyl, hexyloxycarbonyl or heptyloxycarbonyl group.

Phenyl-lower alkoxycarbonyl is, for example, phenyl-$C_1$–$C_4$alkoxycarbonyl, such as benzyl-oxycarbonyl or α-phenylethoxycarbonyl, that is unsubstituted or substituted by $C_1$–$C_4$alkyl, $C_1$–$C_4$alkoxy, hydroxy, halogen and/or by trifluoromethyl.

N-mono- or N,N-di-lower alkylcarbamoyl is, for example, N-mono- or N,N-di-$C_1$–$C_7$alkyl-carbamoyl, preferably N-mono- or N,N-di-$C_1$–$C_4$alkylcarbamoyl, such as especially methyl-carbamoyl, dimethylcarbamoyl or secondly ethylcarbamoyl, diethylcarbamoyl, propylcarbamoyl, dipropylcarbamoyl, isopropylcarbamoyl, diisopropylcarbamoyl, butylcarbamoyl or dibutylcarbamoyl, but may also be isobutylcarbamoyl, sec-butylcarbamoyl, tert-butyl-carbamoyl or a $C_5$–$C_7$alkylcarbamoyl group, such as a pentylcarbamoyl, hexylcarbamoyl or heptylcarbamoyl group.

N-mono- or N,N-di-lower alkylsulfamoyl is, for example, N-mono- or N,N-di-$C_1$–$C_7$alkyl-sulfamoyl, preferably N-mono- or N,N-di-$C_1$–$C_4$alkylsulfamoyl, such as especially methyl-sulfamoyl, dimethylsulfamoyl or secondly ethylsulfamoyl, diethylsulfamoyl, propylsulfamoyl, dipropylsulfamoyl, isopropylsulfamoyl, diisopropylsulfamoyl, butylsulfamoyl or dibutylsulfamoyl, but may also be isobutylsulfamoyl, sec-butylsulfamoyl, tert-butylsulfamoyl or a $C_5$–$C_7$alkylsulfamoyl group, such as a pentylsulfamoyl, hexylsulfamoyl or heptylsulfamoyl group.

Lower alkylene may be straight-chain or branched and may be bonded in any position and is, for example, straight-chain or branched $C_1$–$C_7$alkylene, preferably $C_1$–$C_4$alkylene, such as methylene, ethylene, 1,3- or 1,2-propylene, 1,4-, 1,3- or 2,3-butylene or secondly 1,5-, 1,4- or 2,5-pentylene.

Lower alkenylene may be straight-chain or branched and may be bonded in any position and is, for example, straight-chain or branched $C_2$–$C_7$alkenylene, especially $C_2$–$C_4$alkenylene, such as vinylene, 1,3-prop-2-enylene or 1,4-but-2-enylene.

Carboxy-lower alkylene is, for example, carboxy-$C_1$–$C_4$alkylene, such as carboxymethylene, 1- or 2-carboxyethylene, 1,3-(1-, 2- or 3-carboxy)propylene or 1,4-(1-, 2-, 3- or 4-carboxy)-butylene, but may also be a carboxypentylene or carboxyhexylene group.

Lower alkoxycarbonyl-lower alkylene is, for example, $C_1$–$C_4$alkoxycarbonyl-$C_1$–$C_4$alkylene, such as $C_1$–$C_4$alkoxycarbonylmethylene, 1- or 2-$C_1$–$C_4$alkoxycarbonylethylene, 1,3-(1-, 2- or 3-$C_1$–$C_4$alkoxycarbonyl)propylene or 1,4-(1-, 2-, 3- or 4-$C_1$–$C_4$alkoxycarbonyl)butylene, but may also be a $C_1$–$C_4$alkoxycarbonylpentylene or $C_1$–$C_4$alkoxycarbonylhexylene group. $C_1$–$C_4$Alkoxycarbonyl is, for example, straight-chain ethoxy-, propyloxy-, isopropyloxy- or butyloxy-carbonyl.

Hydroxy-lower alkylene carrying the hydroxy group in a position higher than the α-position to the thio group is, for example, corresponding hydroxy-$C_2$–$C_4$alkylene, such as 1,3-(2-hydroxy)propylene, 1,3-(3-hydroxy)propylene, 1,4-(2-hydroxy)butylene, 1,4-(3-hydroxy)-butylene or 1,4-(4-hydroxy)butylene, but may also be 1,5-(2-hydroxy)pentylene, 1,5-(3-hydroxy)pentylene, 1,5-(4-hydroxy)pentylene or 1,5-(5-hydroxy)pentylene.

Lower alkoxycarbonyl-lower alkylene carrying the lower alkoxy group in a position higher than the α-position is, for example, $C_1$–$C_4$alkoxy-$C_2$–$C_4$alkylene, such as 1,3-(2-$C_1$–$C_4$alkoxy)-propylene, 1,3-(3-$C_1$–$C_4$alkoxy)propylene, 1,4-(2-$C_1$–$C_4$alkoxy)butylene, 1,4-(3-$C_1$–$C_4$alkoxy)-butylene or 1,4-(4-$C_1$–$C_4$alkoxy)butylene, but may also be 1,5-(2-$C_{1-4}$alkoxy)pentylene, 1,5-(3-$C_1$–$C_4$alkoxy) pentylene, 1,5-(4-$C_1$–$C_4$alkoxy)pentylene or 1,5-(5-$C_1$–$C_4$alkoxy)pentylene. $C_1$–$C_4$Alkoxy has, for example, one of the meanings given above and is especially methoxy or ethoxy.

Lower alkenyloxy-lower alkylene or lower alkynyloxy-lower alkylene carrying the lower alkenyloxy or lower alkynyloxy group in a position higher than the α-position is, for example, $C_2$–$C_4$alkenyloxy-$C_3$–$C_4$alkylene, such as 1,3-(3-$C_3$–$C_4$alkenyloxy)propylene, 1,4-(2-$C_3$–$C_4$-alkenyloxy) butylene, 1,4-(3-$C_3$–$C_4$alkenyloxy)butylene or 1,4-(4-$C_3$–$C_4$alkenyloxy)butylene, or $C_2$–$C_4$alkynyloxy-$C_3$–$C_4$alkylene, such as 1,3-(2-$C_3$–$C_4$alkynyloxy)propylene, 1,3-(3-$C_3$–$C_4$alkynyloxy)propylene, 1,4-(2-$C_3$–$C_4$alkynyloxy)butylene, 1,4-(3-$C_3$–$C_4$alkynyloxy) butylene or 1,4-(4-$C_3$–$C_4$alkynyloxy)butylene.

$C_3$–$C_4$alkenyloxy or $C_3$–$C_4$alkynyloxy has, for example, one of the meanings given above and is especially allyloxy, methallyloxy or propargyloxy.

Halogen is, for example, halogen having an atomic number of up to and including 35, such as chlorine or fluorine, and also bromine.

Lower alkanoyl is, for example, $C_1$–$C_7$alkanoyl, especially $C_1$–$C_4$alkanoyl, such as formyl, acetyl, propionyl, butyryl or isobutyryl, but may also be $C_5$–$C_7$alkanoyl, such as pivaloyl.

Tautomers of compounds of formula I are best described by the structural formulae Ia and Ib

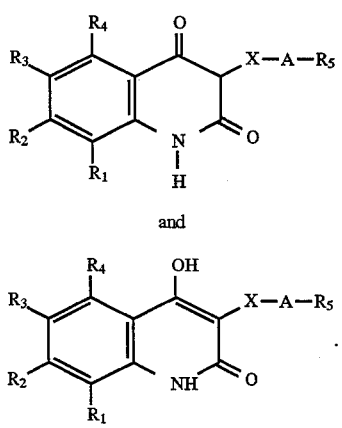

Compounds of formula I wherein at least one of the radicals $R_1$, $R_2$, $R_3$, $R_4$ and $R_5$ is carboxy can form salts with bases or, when at least one further radical of the radicals $R_1$, $R_2$, $R_3$ and $R_4$ is unsubstituted or aliphatically substituted amino, internal salts. Compounds of formula I wherein at least one of the radicals $R_1$, $R_2$, $R_3$ and $R_4$ is unsubstituted or aliphatically substituted amino can form acid addition salts.

Salts of compounds of formula I with bases are, for example, salts thereof with pharmaceutically acceptable bases, such as non-toxic metal salts derived from metals of groups Ia, Ib, Ia and IIb, for example alkali metal salts, especially sodium or potassium salts, alkaline earth metal salts, especially calcium or magnesium salts, and also ammonium salts with ammonia or organic amines or quaternary ammonium bases, such as optionally C-hydroxylated aliphatic amines, especially mono-, di- or tri-lower alkylamines, for example methyl-, ethyl- or diethyl-amine, mono-, di- or tri-(hydroxy-lower alkyl)amines, such as ethanol-, diethanol- or triethanol-amine, tris (hydroxymethyl)methylamine or 2-hydroxy-tert-butyl-amine, or N-(hydroxy-lower alkyl)-N,N-di-lower alkylamines or N-(polyhydroxy-lower alkyl)-N-lower alkylamines, such as 2-(dimethylamino)ethanol or D-glucamine, or quaternary aliphatic ammonium hydroxides, for example tetrabutylammonium hydroxide.

Acid addition salts of compounds of formula I are, for example, the pharmaceutically acceptable salts thereof with suitable mineral acids, such as hydrohalic acids, sulfuric acid or phosphoric acid, for example hydrochlorides, hydrobromides, sulfates, hydrogen sulfates or phosphates, or salts with suitable aliphatic or aromatic sulfonic acids or N-substituted sulfamic acids, for example methanesulfonates, benzenesulfonates, p-toluenesulfonates or N-cyclohexylsulfamates (cyclamates).

Also included are both total and partial salts, that is to say salts with 1,2 or 3, preferably 2, equivalents of base per mole of acid of formula for salts with 1, 2 or 3 equivalents, preferably 1 equivalent, of acid per mole of base of formula I.

For the purposes of isolation or purification it is also possible to use pharmaceutically unacceptable salts. Only the pharmaceutically acceptable, non-toxic salts are used therapeutically, however, and they are therefore preferred.

The compounds of formula I have valuable pharmacological properties. They exhibit a selective non-competitive antagonistic action with respect to N-methyl-D-aspartic-acid-sensitive (NMDA-sensitive) excitatory amino acid receptors of warm-blooded animals. In particular they are capable of binding to strychnine-insensitive glycine modulators of the NMDA-receptor. The binding capacity of the compounds prepared according to the invention and their salts to strychnine-insensitive glycine binding sites of the NMDA-receptor can be determined in vitro, for example in the experimental procedure according to Baron et al., Eur., I. Pharmacol., Molec. Pharmacol. Section 206, pages 149–154 (1991) and Canton et al., J. Pharm. Pharmacol. 44, pages 812–816 (1992) on rat codex and rat hippocampus membranes. In those experimental procedures it is determined to what extent [$^3$H]-5,7-Dichlorkynurensame ($^3$H-DCKA) is displaced the percentual inhibition or, when appropriate, the concentration required for a 50 percent replacement ($IC_{50}$) being assessed. The concentration ($IC_{50}$) required for 50 % displacement lies in the nanomolar and lower millimolar range, that is to say at concentrations of approximately from 0.07 to 1.25 μmol.

By virtue of those properties the compounds of formula I and the pharmaceutically acceptable salts thereof are excellently suitable for the prophylactic and therapeutic treatment of pathological conditions that are responsive to glycine-antagonistic blocking of NMDA-sensitive receptors, for example neurodegenerative disorders, such as those arising from stroke, hypoglycaemia, anoxia or symptoms of cerebral paralysis; ischaemic brain disorders, such as cerebral ischaemia, cerebral ischaemia in cardiosurgery or cardiac arrest, perinatal asphyxia, epileptic fits, Huntingtone's chorea, Alzheimer's disease and Parkinson's disease, amyotrophic lateral sclerosis, spinal and cerebral trauma, and also symptoms of poisoning resulting from neurotoxins or drug abuse; and ischaemic disorders of the eyes; vascular and muscular spasms, such as migraine or local or general spasticity; convulsions, such as epilepsy; and anxiety states and pain such as trigiminus neuralgias.

The anticonvulsive properties of the compounds according to the invention can be determined in vivo, for example, in mice with reference to their pronounced protective action with respect to metrazole-induced convulsions, it being possible to use, for example, the well-established mouse model for metrazole-induced convulsions according to Schmutz et al., Naunyn-Schmiedeberg's Arch. Pharmacol. 342, 61–66 (1990) in which compounds of formula I have a marked protective action in a dosage range of approximately 50 mg/kg and above p.o. and i.p..

The invention relates, for example, to compounds of formula I wherein the radicals $R_1$, $R_2$, $R_3$ and $R_4$ are each independently of the others hydrogen, an aliphatic hydrocarbon radical, free or etherified hydroxy, mercapto or etherified and/or oxidised mercapto, unsubstituted or aliphatically substituted amino, nitro, free or esterified or amidareal carboxy, cyano, free or amidated sulfamoyl, halogen or trifluoromethyl, X is oxy or optionally oxidised thio, A is a divalent aliphatic radical and $R_5$ is aryl or heteroaryl that is unsubstituted or substituted by an aliphatic or aralphatic hydrocarbon radical, by free or etherified hydroxy, by mercapto or etherified and/or oxidised mercapto, by unsubstituted or aliphatically substituted amino, by aliphatic acyl, by free or esterified or amidated carboxy, by cyano, by free or amidated sulfamoyl, by halogen and/or by trifluoromethyl; cyano or free or esterified or amidated carboxy, and their tautomers and/or salts.

The invention relates especially to compounds of formula I wherein the radicals $R_1$, $R_2$, $R_3$ and $R_4$ are each independently of the others hydrogen, lower alkyl, lower alkenyl, lower alkynyl, hydroxy, lower alkoxy, lower alkenyloxy, lower alkynyloxy, mercapto, sulfo, lower alkylthio, lower alkanesulfinyl, lower alkanesulfonyl, lower alkene-sulfonyl, amino, N-mono- or N,N-di-lower alkylamino, nitro, carboxy, lower alkoxycarbonyl; phenyl-lower alkoxycarbonyl that is unsubstituted or substituted by lower alkyl, lower alkoxy, hydroxy, halogen and/or by trifluoromethyl; carbamoyl, N-mono- or N,N-di-lower alkylcarbamoyl, cyano, sulfamoyl, N-mono-or N,N-di-lower alkylsulfamoyl, halogen or trifluoromethyl, X is oxy, thio, sulfinyl or sulfonyl, A is lower alkylene, lower alkenylene, carboxy-lower alkylene, lower alkoxycarbonyl-lower alkylene, hydroxy-lower alkylene carrying the hydroxy group in a position higher than the α-position, lower alkoxy-lower alkylene carrying the lower alkoxy group in a position higher than the α-position, or lower alkenyloxy-lower alkylene carrying the lower alkenyloxy group in a position higher than the α-position, and $R_5$ is a monocyclic or bicyclic aryl radical, a partially hydrogenated bicyclic aryl radical that is preferably bonded via a saturated carbon atom, a monocyclic or bicyclic heteroaryl radical that is bonded via a carbon atom and contains as hetero atom(s) 1, 2, 3 or 4 nitrogen atoms or 1 oxygen or sulfur atom, or a partially hydrogenated bicyclic heteroaryl radical that is preferably bonded via a saturated carbon atom and contains 1 or 2 oxygen or sulfur atoms, each of which is unsubstituted or mono-, di- or tri-substituted by lower alkyl, lower alkenyl, lower alkynyl, phenyl-lower alkyl, hydroxy, lower alkoxy, lower alkenyloxy, lower alkynyloxy, mercapto, sulfo, lower alkylthio, lower alkanesulfinyl, lower alkanesulfonyl, lower alkene-sulfonyl, amino, N-mono- or N,N-di-lower alkylamino, lower alkanoyl, carboxy, lower alkoxycarbonyl; phenyl-lower alkoxycarbonyl that is unsubstituted or substituted by lower alkyl, lower alkoxy, hydroxy, halogen and/or by trifluoromethyl; carbamoyl, N-mono- or N,N-di-lower alkylcarbamoyl, cyano, sulfamoyl, N-mono- or N,N-di-lower alkylsulfamoyl, halogen and/or by trifluoromethyl; carboxy, hydroxymethyl, phenyloxymethyl, lower alkoxycarbonyl, carbamoyl, N-mono- or N,N-di-lower alkylcarbamoyl; N-phenylcarbamoyl or N-phenyl-N-lower alkylcarbamoyl each of which is unsubstituted or substituted in the phenyl moiety by lower alkyl, lower alkoxy, hydroxy, halogen and/or by trifluoromethyl; or cyano, and the tautomers and/or salts thereof.

The invention relates more especially to compounds of formula I wherein the radicals $R_1$, $R_2$, $R_3$ and $R_4$ are each independently of the others hydrogen, $C_1-C_4$alkyl, such as methyl, hydroxy, $C_1-C_4$alkoxy, such as methoxy, mercapto, sulfo, $C_1-C_4$alkylthio, such as methylthio, $C_1-C_4$alkanesulfinyl, such as methanesulfinyl, $C_1-C_4$alkanesulfonyl, such as methanesulfonyl, amino, N-mono- or N,N-di-lower alkylamino, such as dimethyl- or diethyl-amino, nitro, carboxy, $C_1-C_4$alkoxycarbonyl, such as methoxy- or ethoxy-carbonyl; phenyl-$C_1-C_4$alkoxycarbonyl, such as benzyloxycarbonyl or α-phenylethoxycarbonyl, that is unsubstituted or substituted by $C_1-C_4$alkyl, such as methyl, $C_1-C_4$alkoxy, such as methoxy, hydroxy, halogen having an atomic number of up to and including 35, such as chlorine, and/or by trifluoromethyl; carbamoyl, N-mono- or N,N-di-$C_1-C_4$alkylcarbamoyl, such as methyl- or dimethyl-carbamoyl, cyano, sulfamoyl, N-mono- or N,N-di-$C_1-C_4$alkylsulfamoyl, such as methyl- or dimethyl-sulfamoyl, halogen having an atomic number of up to and including 35, such as chlorine, or trifluoromethyl, X is thio, sulfinyl, sulfonyl or secondly oxy, A is, in each case straight-chain, $C_2-C_7$alkylene, especially $C_1-C_4$alkylene, such as methylene, ethylene, 1,3-propylene or 1,4-butylene, $C_2-C_7$alkenylene, especially $C_2-C_4$-alkenylene, such as vinylene, 1,3-prop-2-enylene or 1,4-but-2-enylene, carboxy-$C_1C_4$-alkylene, such as carboxymethylene, 1- or 2-carboxyethylene, 1,3-(1-, 2- or 3-carboxy)-propylene, 1,4-(1-, 2-, 3- or 4-carboxy)butylene, lower alkoxycarbonyl-lower alkylene, such as $C_1C_4$alkoxycarbonylmethylene, 1- or 2-$C_1-C_4$alkoxycarbonylethylene, 1,3-(1-, 2- or 3-$C_1-C_4$alkoxycarbonyl)propylene, 1,4-(1-, 2-, 3- or 4-$C_1-C_4$alkoxycarbonyl)butylene, hydroxy-lower alkylene carrying the hydroxy group in a position higher than the α-position, such as 1,3-(2-hydroxy)propylene, 1,3-(3-hydroxy)propylene, 1,4-(2-hydroxy)butylene, 1,4-(3-$C_1-C_4$hydroxy)butylene and 1,4-(4-hydroxy)butylene, or lower alkoxy-lower alkylene carrying the lower alkoxy group in a position higher than the α-position, such as 1,3-(2-$C_1-C_4$alkoxy)-propylene, 1,3-(3-$C_1-C_4$alkoxy)propylene, 1,4-(2-$C_1-C_4$alkoxy)butylene, 1,4-(3-$C_1-C_4$alkoxy)-butylene and 1,4-(4-$C_1-C_4$alkoxy)butylene, and $R_5$ is a phenyl, naphthyl, indenyl, 1,2,3,4-tetrahydronaphth-1-yl, 1,2,3,4-tetrahydronaphth-2-yl, indan-1-yl, indan-2-yl, pyrrolyl, indolyl, furyl, benzofuranyl, thienyl, benzothienyl, imidazolyl, benzimidazolyl, oxazolyl, benzoxazolyl, thiazolyl, benzthiazolyl, tetrazolyl, pyridyl, quinolinyl, isoquinolinyl, pyrimidinyl, quinazolinyl, pyridazinyl, cinnolinyl, pyrazinyl, quinoxalinyl, triazinyl, chroman-3-yl, chroman-4-yl or 1,4-benzdioxan-2-yl radical that is unsubstituted or mono-, di- or tri-substituted by $C_1-C_4$alkyl, such as methyl, hydroxy, $C_1-C_4$alkoxy, such as methoxy, mercapto, sulfo, $C_1-C_4$alkylthio, such as methylthio, $C_1-C_4$alkanesulfinyl, such as methanesulfinyl, $C_1-C_4$alkanesulfonyl, such as methanesulfonyl, amino, N-mono- or N,N-di-$C_1-C_4$alkylamino, such as dimethyl- or diethyl-amino, nitro, $C_1-C_4$alkanoyl, such as acetyl, carboxy, $C_1-C_4$alkoxycarbonyl, such as methoxy- or ethoxy-carbonyl; phenyl-$C_1-C_4$-alkoxy-carbonyl, such as benzyloxy- or α-phenylethoxy-carbonyl, that is unsubstituted or substituted by $C_1-C_4$alkyl, such as methyl, $C_1-C_4$alkoxy, such as methoxy, hydroxy, halogen having an atomic number of up to and including 35, such as chlorine, and/or by trifluoro-methyl; carbamoyl, N-mono- or N,N-di-$C_1-C_4$alkylcarbamoyl, such as methyl- or dimethyl-carbamoyl, cyano, sulfamoyl, N-mono- or N,N-di-$C_1-C_4$alkylsulfamoyl, such as methyl- or dimethyl-sulfamoyl, halogen having an atomic number of up to and including 35, such as chlorine, and/or by trifluoromethyl; carboxy, hydroxymethyl, phenyloxymethyl, $C_1-C_4$alkoxycarbonyl, such as methoxy- or ethoxy-carbonyl, carbamoyl, N-mono- or N,N-di-$C_1-C_4$alkyl-carbamoyl, such as methyl- or dimethyl-carbamoyl; N-phenylcarbamoyl or N-phenyl-N-$C_1-C_4$alkylcarbamoyl, such as N-phenyl-N-methyl-carbamoyl, each of which is unsubstituted or substituted in the phenyl moiety by $C_1-C_4$alkyl, $C_1-C_4$alkoxy, hydroxy, halogen and/or by trifluoromethyl; or cyano, for example those compounds wherein the radicals $R_1$, $R_2$, $R_3$ and $R_4$ are each independently of the others hydrogen, $C_1-C_4$alkyl, hydroxy, $C_1-C_4$alkoxy, mercapto, sulfo, $C_1-C_4$alkylthio, $C_1-C_4$alkanesulfinyl, $C_1-C_4$alkane-sulfonyl, amino, N-mono-or N,N-di-lower alkylamino, nitro, carboxy, $C_1-C_4$alkoxycarbonyl; phenyl-$C_1-C_4$alkoxycarbonyl that is unsubstituted or substituted by $C_1-C_4$alkyl, $C_1-C_4$alkoxy, hydroxy, halogen having an atomic number of up to and including 35 and/or by trifluoro-methyl; carbamoyl, N-mono- or N,N-di-$C_1-C_4$alkylcarbamoyl, cyano, sulfamoyl, N-mono- or N,N-di-$C_1-C_4$alkylsulfamoyl, halogen having an atomic number of up to and including 35 or trifluoromethyl, X is thio, sulfinyl, sulfonyl or oxy, A is, in each case straight-chain, $C_2$–$C_7$alkylene, carboxy-$C_1$–$C_4$alkylene, $C_1$–$C_4$alkoxy-carbonyl-$C_1$–$C_4$alkylene, hydroxy-lower alkylene carrying the hydroxy group in a position higher than the α-position, or lower alkoxy-lower alkylene carrying the lower alkoxy group in a position higher than the α-position, and $R_5$ is phenyl that is unsubstituted or mono-, di- or tri-substituted by $C_1$–$C_4$alkyl, hydroxy, $C_1$–$C_4$alkoxy, mercapto, sulfo, $C_1$–$C_4$alkylthio, $C_1$–$C_4$alkanesulfinyl, $C_1$–$C_4$alkanesulfonyl, amino, N-mono-or N,N-di-$C_1$–$C_4$alkylamino, nitro, $C_1$–$C_4$alkanoyl, carboxy, $C_1$–$C_4$alkoxy-carbonyl; phenyl-$C_1$–$C_4$alkoxycarbonyl, such as benzyloxy- or cephenylethoxy-carbonyl, that is unsubstituted or substituted by $C_1$–$C_4$alkyl, $C_1$–$C_4$alkoxy, hydroxy, halogen having an atomic number of up to and including 35, such as chlorine, and/or by trifluoromethyl; carbamoyl, N-mono- or N,N-di-$C_1$–$C_4$alkylcarbamoyl, such as methyl- or dimethyl-carbamoyl, cyano, sulfamoyl, N-mono-or N,N-di-$C_1$–$C_4$alkylsulfamoyl, such as methyl- or dimethyl-sulfamoyl, halogen having an atomic number of up to and including 35, such as chlorine, and/or by trifluoromethyl; carboxy, $C_1$–$C_4$alkoxycarbonyl, such as methoxy- or ethoxy-carbonyl, carbamoyl, N-mono- or N,N-di-$C_1$–$C_4$alkylcarbamoyl, such as methyl- or dimethyl-carbamoyl, or cyano, the tautomers and/or salts thereof.

The invention relates especially to compounds of formula I wherein the radicals $R_1$, $R_2$, $R_3$ and $R_4$ are each independently of the others hydrogen, $C_1$–$C_4$alkyl, such as methyl, $C_1$–$C_4$alkoxy, such as methoxy, mercapto, sulfo, nitro, carboxy, $C_1$–$C_4$-alkoxycarbonyl, such as methoxy- or ethoxy-carbonyl, carbamoyl, N-mono- or N,N-di-$C_1$–$C_4$-alkylcarbamoyl, such as methyl- or dimethyl-carbamoyl, cyano, halogen having an atomic number of up to and including 35, such as chlorine, or trifluoromethyl, X is thio, sulfinyl, sulfonyl or secondly oxy, A is, in each case straight-chain, $C_2$–$C_7$alkylene, especially $C_1$–$C_4$alkylene, such as methylene, ethylene, 1,3-propylene or 1,4-butylene, $C_2$–$C_7$alkenylene, especially $C_2$–$C_4$-alkenylene, such as vinylene, 1,3-prop-2-enylene or 1,4-but-2-enylene, carboxy-$C_2$–$C_4$-alkylene, such as 1-carboxyethylene, 1,3-(1-carboxy)propylene or 1,4-(1-carboxy)butylene, $C_1$–$C_4$alkoxycarbonyl-$C_2$–$C_7$alkylene, such as 1-$C_1$–$C_4$alkoxycarbonylethylene, 1,3-(1-$C_1$–$C_4$-alkoxycarbonyl)propylene or 1,4-(1-$C_1$–$C_4$alkoxycarbonyl)butylene, or hydroxy-lower alkylene carrying the hydroxy group in a position higher than the α-position, such as 1,3-(2-hydroxy)propylene, 1,3-(3-hydroxy)propylene or 1,4-(2-hydroxy)butylene, and $R_5$ is a phenyl, naphthyl, 1,2,3,4-tetrahydronaphth-1-yl, 1,2,3,4-tetrahydronaphth-2-yl, thienyl, benzimidazolyl, oxazolyl, benzoxazolyl, thiazolyl, benzthiazolyl, tetrazolyl, pyridyl, quinolinyl, isoquinolinyl, pyrimidinyl, quinazolinyl, chroman-3-yl, chroman-4-yl or 1,4-benzdioxan-2-yl radical that is unsubstituted or mono-, di- or tri-substituted by $C_1$–$C_4$alkyl, such as methyl, hydroxy, $C_1$–$C_4$alkoxy, such as methoxy, $C_1$–$C_4$alkylthio, such as methylthio, $C_1$–$C_4$-alkanesulfinyl, such as methanesulfinyl, $C_1$–$C_4$alkanesulfonyl, such as methanesulfonyl, nitro, $C_1$–$C_4$alkanoyl, such as acetyl, carboxy, $C_1$–$C_4$alkoxycarbonyl, such as methoxy- or ethoxy-carbonyl, carbamoyl, halogen having an atomic number of up to and including 35, such as chlorine, and/or by trifluoromethyl; carboxy, hydroxymethyl, phenyloxymethyl, $C_1$–$C_4$alkoxycarbonyl, such as methoxy- or ethoxy-carbonyl, carbamoyl, N-mono- or N,N-di-$C_1$–$C_4$alkylcarbamoyl, such as methyl- or dimethyl-carbamoyl; N-phenylcarbamoyl or N-phenyl-N-$C_1$–$C_4$alkylcarbamoyl, such as N-phenyl-N-methyl-carbamoyl, each of which is unsubstituted or substituted in the phenyl moiety by $C_1$–$C_4$alkyl, $C_1$–$C_4$alkoxy, hydroxy, halogen and/or by trifluoromethyl; or cyano, and the tautomers and/or salts thereof.

The invention relates preferably to compounds of formula I wherein $R_1$ and $R_3$ are hydrogen, $R_2$ is halogen having an atomic number of up to and including 35, and $R_4$ is hydrogen, halogen having an atomic number of up to and including 35, such as chlorine, $C_1$–$C_4$alkyl, such as ethyl, or nitro, X is thio, A is straight-chain $C_1$–$C_4$alkylene, such as methylene, ethylene or 1,3-propylene, and $R_5$ is phenyl, pyrimidinyl, such as pyrimidin-5-yl, chromanyl, such as chroman-2-yl, 1,4-benzodioxanyl, such as 1,4-benzodioxan-3-yl, thienyl, such as thien-2-yl or thien-3-yl, or 1,2,3,4-tetrahydronaphth-2-yl each of which is unsubstituted or mono- or di-substituted by halogen having an atomic number of up to and including 35, such as chlorine or fluorine, cyano, carboxy, $C_1$–$C_4$alkoxycarbonyl, such as methoxy- or ethoxy-carbonyl, N-$C_1$–$C_4$alkylcarbamoyl, such as methylcarbamoyl, N-phenyl-N-$C_1$–$C_4$alkylcarbamoyl, such as N-phenyl-N-methyl-carbamoyl, hydroxy, $C_1$–$C_4$alkanoyl, such as acetyl, and/or by $C_1$–$C_4$alkyl, such as methyl; carboxy, $C_1$–$C_4$alkoxycarbonyl, such as methoxy- or ethoxy-carbonyl, N-$C_1$–$C_4$alkylcarbamoyl, such as methylcarbamoyl, or N-phenyl-N-$C_1$–$C_4$alkylcarbamoyl, such as N-phenyl-N-methyl-carbamoyl, for example those compounds of formula I wherein $R_1$ and $R_3$ are hydrogen, $R_2$ is halogen having an atomic number of up to and including 35 and $R_4$ is hydrogen or halogen having an atomic number of up to and including 35, X is thio, A is straight-chain $C_1$–$C_4$alkylene and $R_5$ is phenyl that is unsubstituted or mono- or di-substituted by halogen having an atomic number of up to and including 35, such as chlorine, cyano, carboxy, $C_1$–$C_4$alkoxycarbonyl, such as methoxy- or ethoxy-carbonyl, hydroxy, $C_1$–$C_4$alkanoyl, such as acetyl, and/or by $C_1$–$C_4$alkyl, such as methyl; carboxy or $C_1$–$C_4$alkoxycarbonyl, such as methoxy- or ethoxy-carbonyl, and the tautomers and/or salts thereof.

The invention relates especially to compounds of formula I wherein $R_1$ and $R_3$ are hydrogen, $R_2$ is halogen having an atomic number of up to and including 35 and $R_4$ is hydrogen, halogen having an atomic number of up to and including 35, $C_1$–$C_4$alkyl or nitro, X is thio, A is straight-chain $C_1$–$C_4$alkylene and $R_5$ is phenyl that is unsubstituted or substituted by halogen having an atomic number of up to and including 35, such as fluorine, $C_1$–$C_4$alkoxy, such as methoxy, or by carboxy; thienyl, such as thien-2-yl or thien-3-yl, 1,2,3,4-tetrahydronaphth-2-yl, pyrimidin-5-yl, chroman-2-yl, 1,4-benzodioxan-3-yl, carboxy or $C_1$–$C_4$alkoxycarbonyl, such as methoxy- or ethoxy-carbonyl, for example those compounds wherein $R_1$ and $R_3$ are hydrogen, $R_2$ is halogen having an atomic number of up to and including 35 and $R_4$ is hydrogen, $C_1$–$C_4$alkyl, such as methyl, or halogen having an atomic number of up to and including 35, such as chlorine, X is thio, A is straight-chain $C_1$–$C_4$alkylene, such as methylene, ethylene or 1,3-propylene, and $R_5$ is phenyl that is unsubstituted or substituted by halogen having an atomic number of up to and including 35, such as chlorine; carboxy or $C_1$–$C_4$alkoxycarbonyl, such as methoxy- or ethoxy-carbonyl, and the tautomers and/or salts thereof.

The invention relates specifically to the compounds of formula I mentioned in the Examples and the salts thereof, especially the pharmaceutically acceptable salts thereof.

The process for the preparation of the novel compounds of formula I is based on methods known per se and is carried out, for example, as follows:

a compound of formula II

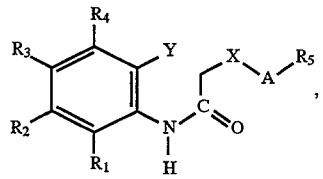

wherein

Y is a reactive carboxy function, is cyclised intramolecularly and, if desired, a resulting compound is converted into a different compound of formula I, a mixture of isomers obtainable in accordance with the process is separated into the components and the preferred isomer is isolated, and/or a free compound obtainable in accordance with the process is converted into a salt or a salt obtainable in accordance with the process is converted into the corresponding free compound.

Reactive carboxy functions are, for example, carboxy functions present in an ester form, anhydride form or amide form, such as lower alkoxycarbonyl, for example methoxy- or ethoxy-carbonyl, or unsubstituted or substituted benzyloxycarbonyl, lower alkanoyl-oxycarbonyl, such as formyloxy- or acetoxy-carbonyl, halocarbonyl, for example chloro-carbonyl, or unsubstituted or substituted carbamoyl, for example carbamoyl, dimethyl-carbamoyl, piperidinocarbonyl, thiomorpholinocarbonyl or morpholinocarbonyl, as well as N-lower alkoxycarbamoyl, such as N-methoxycarbamoyl, or N-lower alkoxy-N-lower alkyl-carbamoyl, such as N-methoxy-N-methyl-carbamoyl.

The intramolecular cyclisation of compounds of formula II is carried out in customary manner, preferably in the presence of a metal base, such as an unsubstituted or lower alkylated or silylated alkali metal amide, for example sodium amide, or an alkali metal di-lower alkylamide or preferably alkali metal bis-tri-lower alkylsilyl-amide, especially lithium, sodium or potassium bis-trimethylsilyl-amide, in an inert organic solvent, such as tetrahydro-furan, dioxane or dimethylformamide, if necessary with cooling, for example in a temperature range of approximately from –25° to +20°, preferably from –5° to +5°, and with mildly acidic working-up, for example treatment with a dilute, aqueous mineral acid, such as 1N to 3N hydrochloric acid.

The starting materials can be prepared in accordance with processes known per se, for example by condensing a compound of formula III

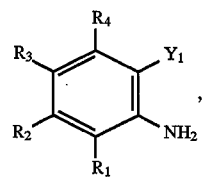

wherein $Y_1$ has one of the meanings given for Y or is carboxy, in customary manner first with a reactive derivative, such as an anhydride or halide, of a haloacetic acid, for example with bromoacetic acid bromide, and then with a compound of formula IV

wherein X, A and $R_5$ are as defined.

Compounds obtainable in accordance with the process can be converted into other compounds of formula I in customary manner.

For example, compounds of formula I wherein X is thio or at least one of the radicals $R_1$, $R_2$, $R_3$ and $R_4$ is etherified mercapto can be oxidised in customary manner, for example by treatment with m-chloroperbenzoic acid, to form the corresponding compounds of formula I wherein X is sulfinyl or sulfonyl or at least one of the radicals $R_1$, $R_2$, $R_3$ and $R_4$ is oxidised etherified mercapto.

Resulting salts can be converted into the free compounds in a manner known per se, for example by treatment with a base, such as an alkali metal hydroxide, a metal carbonate or metal hydrogen carbonate, or another of the salt-forming bases mentioned at the beginning, or with an acid, such as a mineral acid, for example with hydrochloric acid, or another of the salt-forming acids mentioned at the beginning.

Resulting salts can be converted into different salts in a manner known per se; acid addition salts, for example, by treatment with a suitable metal salt, such as a sodium, barium or silver salt, of a different acid in a suitable solvent in which an inorganic salt being formed is insoluble and is therefore eliminated from the reaction equilibrium, and basic salts by freeing of the free acid and conversion into a salt again.

The compounds of formula I, including their salts, may also be obtained in the form of hydrates or may include the solvent used for crystallisation.

As a result of the close relationship between the novel compounds in free form and in the form of their salts, hereinabove and hereinbelow any reference to the free compounds and their salts is to be understood as including also the corresponding salts and free compounds, respectively, as appropriate and expedient.

Resulting diastereoisomeric mixtures and mixtures of racemates can be separated into the pure diastereoisomers or racemates in known manner on the basis of the physico-chemical differences between the constituents, for example by chromatography and/or fractional crystallisation.

Resulting racemates can also be resolved into the optical antipodes in accordance with known methods, for example by recrystallisation from an optically active solvent, with the aid of microorganisms or by reaction of the resulting diastereoisomeric mixture or racemate with an optically active auxiliary compound, for example depending on the acidic, basic or functionally modifiable groups present in compounds of formula I, with an optically active acid, base or an optically active alcohol, into mixtures of diastereoisomeric salts or functional derivatives, such as esters, and separation thereof into the diastereoisomers from which the desired enantiomer can be freed in the appropriate customary manner. Bases, acids and alcohols suitable for that purpose are, for example, optically active alkaloid bases, such as strychnine, cinchonine or brucine, or D- or L-(1-phenyl) ethylamine, 3-pipecoline, ephedrine, amphetamine and similar synthetically obtainable bases, optically active carboxylic or sulfonic acids, such as quinic acid or D- or L-tartaric acid, D- or L-di-toluyltartaric acid, D- or L-malic acid, D- or L-mandelic acid or D- or L-camphorsulfonic acid, and optically active alcohols, such as borneol or D- or L-(1-phenyl)ethanol.

The invention relates also to those forms of the process according to which a compound obtainable as intermediate at any stage of the process is used as starting material and the remaining steps are carried out or a starting material is used in the form of a salt or, especially, is formed under the reaction conditions.

The invention relates also to novel starting materials, which have been developed specifically for the preparation of the compounds according to the invention, especially the group of starting materials that result in the compounds of formula I described at the beginning as being preferred, to the processes for their preparation and to their use as intermediates.

The invention relates also to pharmaceutical compositions comprising the compounds according to the invention or pharmaceutically acceptable salts thereof as active ingredients, and to processes for the preparation thereof.

The pharmaceutical compositions according to the invention, which comprise the compound according to the invention or pharmaceutically acceptable salts thereof, are for enteral, such as oral and also rectal, and parenteral administration to (a)warm-blooded animal(s), the compositions comprising the pharmacological active ingredient alone or together with a pharmaceutically acceptable carrier. The daily dose of the active ingredient depends upon age and individual condition and upon the mode of administration.

The novel pharmaceutical compositions comprise, for example, from approximately 10% to approximately 80%, preferably from approximately 20% to approximately 60%, active ingredient. Pharmaceutical compositions according to the invention for enteral or parenteral administration are, for example, those in unit dose forms, such as dragées, tablets, capsules or suppositories, and also ampoules. They are prepared in a manner known per se, for example by means of conventional mixing, granulating, confectioning, dissolving or lyophilising processes. For example, pharmaceutical compositions for oral administration can be obtained by combining the active ingredient with solid carders, optionally granulating a resulting mixture, and processing the mixture or granules, if desired or necessary, after the addition of suitable excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose and/or polyvinylpyrrolidone, if desired disintegrators, such as the above-mentioned starches, and also carboxymethyl starch, cross-linked polyvinylpyrrolidone, agar, alginic acid or a salt thereof, such as sodium alginate. Excipients are especially flow agents, flow-conditioners and lubricants, for example silicic acid, talc, stearic acid or salts thereof, such as magnesium or calcium stearate, and/or polyethylene glycol. Dragée cores are provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures or, for the preparation of enteric coatings, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredient.

Other orally administrable pharmaceutical compositions are hard gelatin capsules and also soft, sealed capsules consisting of gelatin and a plasticiser, such as glycerol or sorbitol. The hard gelatin capsules may comprise the active ingredient in the form of granules, for example in admixture with fillers, such as lactose, binders, such as starches, and/or gildants, such as talc or magnesium stearate, and if desired stabilisers. In soft capsules the active ingredient is preferably dissolved or suspended in suitable liquids, such as fatty oils, paraffin oil or liquid polyethylene glycols, it likewise being possible to add stabilisers.

Suitable rectally administrable pharmaceutical compositions are, for example, suppositories that consist of a combination of the active ingredient with a suppository base material. Suitable suppository base materials are, for example, natural or synthetic triglycerides, paraffin hydrocarbons, polyethylene glycols or higher alkanols. It is also possible to use gelatin rectal capsules which comprise a combination of the active ingredient with a base material. Suitable base materials are, for example, liquid triglycerides, polyethylene glycols or paraffin hydrocarbons.

For parenteral administration there are suitable, especially, aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions which comprise viscosity-increasing substances, for example sodium carboxymethylcellulose, sorbitol and/or dextran, and optionally also stabilisers.

The dosage of the active ingredient depends upon the species of warm-blooded animal, age and individual condition and also upon the mode of administration. In a normal case the approximate daily dose for oral administration to a patient weighing about 75 kg is estimated to be from approximately 10 mg to approximately 500 mg.

The following Examples serve to illustrate the invention; temperatures are given in degrees Celsius, pressures in mbar.

EXAMPLE 1

2 g (5.3 mmol) of 4-chloro-N-(3-phenylpropylthio)acetyl-anthranilic acid methyl ester are placed in 20 ml of tetrahydrofuran at 0°. A 1-molar tetrahydrofuran solution of sodium bis-trimethylsilylamide is added dropwise thereto. The mixture is then stirred for 20 minutes at 0° and for 2 hours at room temperature. The reaction mixture is poured into 200 ml of 2N hydrochloric acid/ice and the resulting white suspension is filtered off. The resulting colourless crystals are made into a suspension in ethanol and stirred for 2 hours. The mixture is filtered, followed by washing with ethanol and diethyl ether. After drying, 7-chloro-4-hydroxy-3-(3-phenylpropylthio)-2(1H)-quinolone is obtained in the form of colourless crystals having a melting point of 184°–186°.

The starting material can be prepared as follows:

10 g (53.9 mmol) of 4-chloroanthranilic acid methyl ester are dissolved in 400 ml of toluene and at room temperature 5.4 ml (62 mmol) of bromoacetyl bromide are added dropwise thereto. The mixture is heated to reflux and then stirred for 4 hours. The reaction mixture is cooled to room temperature and extracted with saturated sodium hydrogen carbonate solution, water and brine. The aqueous phases are washed with toluene, and the organic phases are combined, dried over sodium sulfate, filtered and concentrated by evaporation. Chromatography on silica gel with ethyl acetate yields 4-chloro-N-(bremoacetyl)-anthranilic acidic methyl ester in the form of colourless crystals having a melting point of 95°–96°.

4.3 g (28.7 mmol) of 3-phenylpropylthiol are added dropwise at 0° to a mixture of 1.4 g (31.6 mmol) of sodium hydride dispersion in oil (55%) and 30 ml of tetrahydrofuran. The mixture is then stirred for 30 minutes at 0°. A solution of 4-chloro-N-(bromoacetyl)-anthranilic acid methyl ester in 30 ml of tetrahydrofuran is added dropwise and the mixture is then stirred for one hour at 0° and for three hours at room temperature. Ethyl acetate is added and the reaction mixture is extracted with water and brine. The aqueous phases are washed with ethyl acetate and the organic phases are combined, dried over sodium sulfate, filtered and concentrated by evaporation. Chromatography on silica gel with hexane/ethyl acetate (4:1) yields 4-chloro-N-(3-phenylpropylthio)acetylanthranilic acid methyl ester in the form of a yellow oil.

EXAMPLE 2

Cyclisation of 4-chloro-6-ethyl-N-(3-phenylpropylthioacetyl)-anthranilic acid methyl ester by means of sodium N,N-bis(trimethylsilyl)amide in tetrahydrofuran yields 7-chloro-5-ethyl-4-hydroxy-3-(3-phenylpropylthio)-2(1H)-quinolone having a melting point of 183°–185°.

The starting material can be prepared, for example, by reaction of 6-ethyl-4-chloro-N-bromoacetyl-anthranilic acid methyl ester with 3-phenylpropylthiol in the presence of sodium hydride.

EXAMPLE 3

Cyclisation of 4-chloro-N-(2-phenethylthioacetyl)-anthranilic acid methyl ester by means of sodium N,N-bis(trimethylsilyl)amide in tetrahydrofuran yields 7-chloro-4-hydroxy-3-(2-phenethylthio)-2(1H)-quinolone having a melting point of 213°–215°.

EXAMPLE 4

Cyclisation of 4-chloro-6-(hex-1-enyl)-N-(3-phenylpropylthioacetyl)-anthranilic acid methyl ester by means of sodium N,N-bis(trimethylsilyl)amide in tetrahydrofuran yields 7-chloro-5-(hex-1-enyl)-4-hydroxy-3-(3-phenylpropylthio)-2(1H)-quinolone having a melting point of 145°–148°.

The starting material can be prepared, for example, by reaction of 4-chloro-6-iodo-N-bromo-acetyl-anthranilic acid methyl ester with hexen-1-yl-tributylstannane in the presence of tri-phenylphosphine palladium chloride and lithium chloride in dimethylformamide and subsequent reaction of the 4-chloro-6-(hex-1-enyl)-N-bromoacetyl-anthranilic acid methyl ester so obtainable with 3-phenylpropylthiol in the presence of sodium hydride.

EXAMPLE 5

Cyclisation of 4,6-dichloro-N-[3-(4-methoxycarbonylphenyl)propylthioacetyl]-anthranilic acid methyl ester by means of sodium N,N-bis(trimethylsilyl)amide in tetrahydrofuran yields 5,7-dichloro-4-hydroxy-3-[3-(4-methoxycarbonylphenyl)propyethio]-2(1H)-quinolone and hydrolysis thereof by means of 2N sodium hydroxide solution yields 5,7-di-chloro-4-hydroxy-3-[3-(4-carboxyphenyl)propylthio]-2(1H)-quinolone having a melting point of 275°–277°.

The starting material can be prepared, for example, by reaction of 4,6-dichloro-N-bromo-acetyl-anthranilic acid methyl ester with 3-(4-methoxycarbonylphenyl)propylthiol (obtainable from the bromide) in the presence of sodium hydride.

EXAMPLE 6

Cyclisation of 4,6-dichloro-N-[3-(3-methoxycarbonylphenyl)propylthioacetyl]-anthranilic acid methyl ester by means of sodium N,N-bis(trimethylsilyl)amide in tetrahydro-furan yields 5,7-dichloro-4-hydroxy-3-[3-(3-methoxycarbonylphenyl)propylthio]-2(1H)-quinolone and hydrolysis thereof by means of 2N sodium hydroxide solution yields 5,7-di-chloro-4-hydroxy-3-[3-(3-carboxyphenyl)propylthio]-2(1H)-quinolone having a melting point of 269°–272°.

The starting material can be prepared, for example, by reaction of 4,6-dichloro-N-bromo-acetyl-anthranilic acid methyl ester with 3-(3-methoxycarbonylphenyl)propylthio (obtainable from the bromide) in the presence of sodium hydride.

EXAMPLE 7

2.0 g (6.03 mmol) of 4-chloro-N-(methoxycarbonylmethylthioacetyl)-anthranilic acid methyl ester are placed in 20 ml of tetrahydrofuran at 0°, and 290 mg (6.63 mmol) of sodium hydride dispersion in oil (55%) are added. The mixture is stirred for 15 minutes at 0° and for 3 hours at room temperature. The reaction mixture is then poured onto ice-water, adjusted to pH 3 with 1N hydrochloric acid and extracted with ethyl acetate. The organic phases are combined, dried with sodium sulfate, filtered and concentrated. 7-chloro-4-hydroxy-3-(methoxycarbonylmethylthio)-2(1H)-quinolone is obtained which can be characterised as an acid in accordance with Example 8.

The starting material can be prepared as follows:

21.24 g (0.114 mol)of 4-chloroanthranilic acid methyl ester and 19.1 ml (0.137 mol) of tri-ethylamine are placed in 180 ml of methylene chloride at 0°. A solution of 20.9 g (0.114 mol) of 2-(chloroformylmethylthio)-acetic acid methyl ester in 20 ml of methylene chloride is added dropwise and the mixture is stirred for 15 minutes at 0° and for 3 hours at room temperature. The reaction mixture is extracted with water and brine and the aqueous phases are washed with methylene chloride. The organic phases are combined, dried with sodium sulfate, filtered and concentrated. Chromatography of the crude product on silica gel with hexane/ethyl acetate (4:1) yields, in the form of yellowish crystals, 4-chloro-N-(methoxycarbonylmethylthioacetyl)anthranilic acid methyl ester which is still impure.

EXAMPLE 8

The 7-chloro-4-hydroxy-3-(methoxycarbonylmethylthio)-2(1H)-quinolone obtained in accordance with Example 7 is dissolved in 2N sodium hydroxide solution and left to stand for 2 hours at room temperature. The reaction mixture is adjusted to pH 2 with 4N hydrochloric acid and the resulting suspension is filtered. The colourless crystals are dried under a high vacuum at 60°. 7-chloro-4-hydroxy-3-(carboxymethylthio)-2(1H)-quinolone is obtained in the form of pure crystals having a melting point of 288° (decomp.).

EXAMPLE 9

2.0 g (6.03 mmol) of 4-chloro-N-(methoxycarbonylthio) acetyl-anthranilic acid methyl ester are placed in 20 ml of tetrahydrofuran at 0°, and 290 mg (6.63 mmol) of sodium hydride dispersion in oil (55%) are added. The mixture is stirred for 15 minutes at 0° and for 3 hours at room temperature. The reaction mixture is then poured into icewater, adjusted to pH 3 with 1N hydrochloric acid and extracted with ethyl acetate. The organic phases are combined, dried with sodium sulfate, filtered and concentrated. The intermediate is dissolved in 2N sodium hydroxide solution and left to stand for 2 hours at room temperature. The reaction mixture is adjusted to pH 2 with 4N hydrochloric acid and the resulting suspension is filtered. The colourless crystals are dried under a high vacuum at 60°. 7-chloro-4-hydroxy-3-(carboxymethylthio)-2(1H)-quinolone is obtained in the form of pure crystals having a melting point of 288° (decomp.).

The starting material can be prepared, for example, as follows:

21.24 g (0.114 mol) of 4-chloroanthranilic acid methyl ester and 19.1 ml (0.137 mol) of triethylamine are placed in 180 ml of methylene chloride at 0°. A solution of 20.9 g (0.114 mol) of 2-(chloroformylmethylthio)-acetic acid methyl ester (T. Terasawa and T. Okada, J. Org. Chem., 42, 1163 (1977)) in 20 ml of methylene chloride is added dropwise thereto and the mixture is then stirred for 15 minutes at 0° and for 3 hours at room temperature. The reaction mixture is extracted with water and brine and the aqueous phases are washed with methylene chloride. The organic phases are combined, dried with sodium sulfate, filtered and concentrated. Chromatography of the crude product on silica gel with hexane/ethyl acetate (4:1) yields, in the form of yellowish crystals, 4-chloro-N-(methoxycarbonylmethylthio)acetylanthranilic acid methyl ester which is still impure.

EXAMPLE 10

Cyclisation of 4,6-dichloro-N-(1-methoxycarbonylmethylthioacetyl)-anthranilic acid methyl ester by means of sodium N,N-bis(trimethylsilyl)amide in tetrahydrofuran and subsequent hydrolysis by means of 2N sodium hydroxide solution yields 5,7-dichloro-4-hydroxy-3-(carboxymethylthio)-2(1H)-quinolone having a melting point of >300°.

EXAMPLE 11

2.0 g (5.6 mmol) of 4-chloro-N-(3-methoxycarbonylpropylthio)acetyl-anthranilic acid methyl ester are placed in 20 ml of tetrahydrofuran at 0°, and 16.8 ml of a 1M solution of sodium bis-trimethylsilylamide are added dropwise thereto. The mixture is then stirred for 30 minutes at 0° and the reaction mixture Is then poured into 2N hydrochloric acid/ice. The resulting white suspension is filtered with suction and the resulting colourless crystals are dried under a high vacuum at 60°. The dried product is made into a suspension in ethyl acetate and stirred for 30 minutes. The suspension is filtered, and the colourless crystals are dried under a high vacuum at 70°, yielding 7-chloro-4-hydroxy-3-(3-methoxycarbonyl-propylthio)-2(1H)-quinolone in the form of colourless crystals having a melting point of 183°–185° (decomp.).

The starting material can be prepared, for example, as follows:

3.5 g (26.1 mmol) of 4-thiobutyric acid methyl ester are added dropwise to a suspension of 1.4 g (31.3 mmol) of sodium hydride dispersion in oil (55%), and 20 ml of tetrahydrofuran. The mixture is then stirred for 20 minutes at room temperature, and then a solution of 6.3 g of N-bromoacetyl-4-chloro-anthranilic acid methyl ester in 60 ml of tetrahydrofuran is added dropwise thereto and the mixture is stirred for a further two hours at room temperature. Ethyl acetate is added and the reaction mixture is then extracted with water and brine. The aqueous phases are washed with ethyl acetate, and the organic phases are combined, added with sodium sulfate, filtered and concentrated. Chromatography of the crude product on silica gel with hexane/ethyl acetate (3:1) yields impure 4-chloro-N-(3-methoxycarbonyl-propylthio)-acetylanthranilic acid methyl ester in the form of colourless crystals having a melting point of 57°–59°.

EXAMPLE 12

895 mg (2.73 mmol) of 7-chloro-4-hydroxy-3-(3-methoxycarbonylpropylthio)-2(1H)-quinolone are dissolved in 10 ml of 2N sodium hydroxide solution and the resulting solution is stirred for one hour at room temperature. The reaction mixture is adjusted to pH 2 with concentrated hydrochloric acid and the resulting white suspension is filtered and washed with water. The resulting colourless crystals are dried under a high vacuum at 70°, yielding 3-(3-carboxypropylthio)-7-chloro-4-hydroxy-2(1H)-quinolone in the form of colourless crystals having a melting point of 239°–241° (decomp.).

EXAMPLE 13

6.3 g (16.12 mmol) of 4-chloro-N-(4-phenylbutylthio) acetyl-anthranilic acid methyl ester are placed in 60 ml of tetrahydrofuran at 0°, and 48.3 ml of a 1-molar solution of sodium bis-trimethylsilylamide are added dropwise thereto. The mixture is then stirred for 30 minutes at room temperature. The reaction mixture is poured into 200 ml of 2N hydrochloric acid/ice and the resulting white suspension is filtered with suction and the colourless crystals are dried under a high vacuum at 60°. 7-chloro-3-(4-phenylbutylthio)-4-hydroxy-2(1H)-quinolone is obtained in the form of colourless crystals having a melting point of 176°.

The starting material can be prepared, for example, as follows:

3.57 g (47.1 mmol) of thiourea are heated at reflux in 11 ml of ethanol, and a solution of 10 g (46.9 mmol) of 4-phenylbutyl bromide in 23 ml of ethanol is added dropwise thereto. The reaction mixture is maintained at reflux for 4 hours, then cooled and concentrated by evaporation. The crude product is recrystallised from tetrahydrofuran and diethyl ether. S-(4-phenylbutyl)isothiuronium bromide is obtained in the form of crystals that are not completely pure.

11 g (44.1 mmol) of S-(4-phenylbutyl)isothiuronium bromide are placed in 68 ml of water, and a warm solution of 3.71 g (92.7 mmol) of sodium hydroxide in 14 ml of water is added dropwise thereto. The reaction mixture is saturated with sodium chloride and extracted with ether. The organic phases are combined, dried with sodium sulfate, filtered and concentrated. 4-Phenylbutylthiol is obtained in the form of a colourless liquid which is reacted further in the crude state.

1.85 g (42.5 mmol) of sodium hydride dispersion in oil (55%) are placed in 45 ml of tetra-hydrofuran at 0°, and 6.4 g (38.6 mmol) of 4-phenylbutylthiol are added dropwise thereto. The mixture is then stirred for 30 minutes at 0° and then a solution of 10.76 g (35.1 mmol) of N-bromoacetyl-4-chloro-anthranilic acid methyl ester in 45 ml of tetrahydrofuran is added dropwise thereto. The mixture is stirred for one hour at 0° and for 1.5 hours at room temperature. Ethyl acetate is added and the reaction mixture is then extracted with water and brine, and the aqueous phases are washed with ethyl acetate. The organic phases are combined, added with sodium sulfate, filtered and concentrated. Chromatography of the crude product on silica gel yields 4-chloro-N-(4-phenylbutylthio)acetylanthranilic acid methyl ester in the form of a yellow oil.

EXAMPLE 14

0.3 g (6.9 mmol) of sodium hydride dispersion in oil (55%) is placed in 15 ml of tetrahydrofuran at 0°. A solution of 2.2 g (6.3 mmol) of N-(benzylthio)acetyl-4-chloro-anthranilic acid methyl ester in 5 ml of tetrahydrofuran is then added dropwise thereto. The mixture is then stirred for 24 hours at room temperature. The reaction mixture is poured into ice-water, adjusted to pH 3 with 2N hydrochloric acid and extracted with ethyl acetate. The organic phases are washed with water and brine, combined, added with sodium sulfate, filtered with suction and concentrated. Crystallisation of the; crude product from ethyl acetate/hexane yields, after drying, 7-chloro-3-(benzylthio)-4-hydroxy-2(1H)-quinolone in the form of colourless crystals having a melting point of 228°–230°.

The starting material can be prepared, for example, as follows:

5.1 g (27.4 mmol) of 4-chloro-anthranilic acid methyl ester and 5.73 ml (41.1 mmol) of tri-ethylamine are placed in 40 ml of methylene chloride, and a solution of 5.5 g (27.4 mmol) of benzylthioacetyl chloride in 5 ml of methylene chloride is added dropwise thereto. The mixture is then stirred at room temperature for one hour. The reaction mixture is extracted with water and brine. The aqueous phases are then washed with methylene chloride. The organic phases are combined, dried with sodium sulfate, filtered and concentrated. Chromatography of the crude product on silica gel with hexanelethyl acetate (6:1) yields N-(benzylthio)acetyl-4-chloroanthranilic acid methyl ester in the form of a yellow oil.

EXAMPLE 15

1.0 g (2.73 mmol) of N-(benzylsulfinyl)acetyl-4-chloro-anthranilic acid methyl ester is placed in 10 ml of tetrahydrofuran at 0°, and 0.13 g (3 mmol) of sodium hydride dispersion in oil (55%) is added thereto. The mixture is then stirred for 15 minutes at 0° and for 2 hours at room temperature. Water is added and the reaction mixture is then adjusted to pH 2–3 with 1N hydrochloric acid and extracted with ethyl acetate. The organic phases are washed with water and brine, combined, dried with sodium sulfate, filtered and concentrated. Crystallisation of the crude product from ethyl acetate/petroleum ether yields 7-chloro-3-(benzylsulfinyl)-4-hydroxy-2(1H)-quinolone in the form of colourless crystals having a melting point of 234° (decomp.).

The starting material can be prepared, for example, as follows:

2 g (5.7 mmol) of N-(benzylthio)acetyl-4-chloro-anthranilic acid methyl ester and 3.66 g (17.1 mmol) of sodium metaperiodate are dissolved in 12 ml of water and 48 ml of acetone and the resulting solution is stirred at reflux for 6 hours. The reaction mixture is allowed to cool, filtered and concentrated by evaporation. Chromatography of the crude product on silica gel with hexane/ethyl acetate yields N-(benzylsulfinyl)acetyl-4-chloro-anthranilic acid methyl ester in the form of a yellow oil interspersed with crystals.

EXAMPLE 16

In a manner analogous to that described in Examples 1 to 15 it is possible to prepare, by cyclisation of 4-chloro-N-[1-(1-methoxycarbonyl-3-phenyl-propyl)thioacetyl]-anthranilic acid methyl ester, 7-chloro-4-hydroxy-3-(1-methoxycarbonyl-3-phenyl-propylthio)-2(1H)-quinolone and, by subsequent hydrolysis thereof, 7-chloro-4-hydroxy-3-(1-carboxy-3-phenyl-propylthio)-2(1H)-quinolone having a melting point of 262°–266°.

The starting material can be prepared, for example, as follows:

2.3 g (53.2 mmol) of sodium hydride in the form of a suspension in mineral oil are placed at 0° in 30 ml of tetrahydrofuran. Then at 0° to 10°, 6.6 g (44.:3 mmol) of thioglycolic acid tert-butyl ester are added dropwise thereto. A viscous suspension is formed which is diluted with 50 ml of tetrahydrofuran. The mixture is then stirred for 20 minutes at 0° and then 12 g (44.3 mmol) of 2-bromo-4-phenyl-butyric acid methyl ester are added dropwise thereto. The mixture is stirred for 2 hours at room temperature, then taken up in 100 ml of ethyl acetate and extracted by shaking in succession with 50 ml of water and 50 ml of saturated sodium chloride solution. The aqueous phases are combined and extracted by shaking with 25 ml of ethyl acetate. The organic phases are combined, dried over sodium sulfate, filtered and concentrated by evaporation. Chromatography on silica g al with hexane/ethyl acetate (20:1) as eluant yields 5.7 g (38% of theory) of 2-tert-butyloxycabonylmethylthio-4-phenyl-butyric acid ethyl ester in the form of an oil.

5.6 g (16.5 mmol) of 2-tert-butyloxycarbonylmethylthio-4-phenyl-butyric acid ethyl ester are placed at room temperature in 60 ml of dichloromethane. 3.8 ml (49.6 mmol) of trifluoro-acetic acid are added and the mixture is stirred for 16 hours at room temperature, then a further 3.8 ml of trifluoroacetic acid is added and the mixture is stirred for 24 hours at room temperature and then washed in succession with 25 ml of water and 25 ml of saturated sodium chloride solution. The aqueous phases are then washed with 2550 ml of dichloro-methane. The combined organic phases are dried over sodium sulfate, filtered and concentrated by evaporation. 4.86 g (100% of theory) of crude 2-carboxymethylthio-4-phenyl-butyric acid ethyl ester are obtained in the form of a brown oil.

4.6 g (16.3 mmol) of 2-carboxymethylthio-4-phenyl-butyric acid ethyl ester and 1.8 ml (16.3 mmol) of 4-methylmorpholine are placed under nitrogen at 0° in 100 ml of dichloro-methane. Then 2.1 ml (16.3 mmol) of chloroformic acid butyl ester are added dropwise thereto. The mixture is stirred for 30 minutes at 0°; 3 g (16.3 mmol) of 4-chloroanthranilic acid methyl ester are added and the mixture is then stirred for 16 hours and concentrated by evaporation. Chromatography on silica gel with hexanemethyl acetate (7:1) as eluant yields 1.47 g (20% of theory) of 4-chloro-N-[1-(1-methoxycarbonyl-3-phenyl-propyl)thioacetyl]-anthranilic acid methyl ester in the form of a yellowish oil.

EXAMPLE 17

Cyclisation of 4-chloro-N-[1-(2-acetoxy-3-phenyl-propyl)thioacetyl]-anthranilic acid methyl ester by means of sodium N,N-bis(trimethylsilyl)amide in tetrahydrofuran and subsequent hydrolysis by means of 2N sodium hydroxide solution yield 7-chloro-4-hydroxy-3-(2-hydroxy-3-phenyl-propylthio)-2(1H)-quinolone having a melting point of 158°–160°.

The starting material can be prepared, for example, as follows:

8 g (37.2 mmol) of 2-hydroxy-3-phenyl-propyl bromide are dissolved at room temperature in 80 ml of dichloromethane; with stirring, 2.64 ml (37.2 mmol) of acetyl chloride and after 3 hours a further 2.64 ml (37.2 mmol) of acetyl chloride are added dropwise thereto; the mixture is stirred for 4 hours at 60° and for 16 hours at room temperature and washed with 25 ml each of water and saturated sodium chloride solution. The aqueous phases are combined and washed with 30 ml of dichloromethane. The combined organic phases are dried over sodium sulfate and concentrated by evaporation. Chromatography on silica gel with hexane/ethyl acetate (19:1) as eluant yields 8.03 g (83% of theory) of 2-acetoxy-3-phenyl-propyl bromide in the form of a colourless liquid.

2-Acetoxy-3-phenyl-propylthioacetic acid tert-butyl ester is obtained from 2-acetoxy-3-phenylpropyl bromide by condensation with thioglycolic acid tert-butyl ester in the presence of sodium hydride.

Treatment of 2-acetoxy-3-phenyl-propylthioacetic acid tert-butyl ester with trifluoroacetic acid yields 2-acetoxy-3-phenyl-propylthioacetic acid and treatment thereof with phosgene yields 2-acetoxy-3-phenyl-propylthioacetyl chloride.

4-Chloro-N-[1-(2-acetoxy-3-phenyl-propyl)thioacetyl]-anthranilic acid methyl ester is obtained from 2-acetoxy-3-phenyl-propylthioacetyl chloride by reaction with 4-chloro-anthranilic acid methyl ester.

EXAMPLE 18

Cyclisation of 4-chloro-N-[1-(2-acetoxyethyl)thioacetyl]-anthranilic acid methyl ester by means of sodium N,N-bis(trimethylsilyl)amide in tetrahydrofuran and subsequent hydrolysis by means of 2N sodium hydroxide solution yields 7-chloro-4-hydroxy-3-(2-hydroxyethylthio)-2(1H)-quinolone having a melting point of 233°–236°.

The starting material can be prepared, for example, by reaction of 4-chloro-N-bromoacetyl-anthranilic acid methyl ester with 2-acetoxyethylthiol in the presence of sodium hydride.

EXAMPLE 19

In a manner analogous to that described in Example 15, 7-chloro-3-(benzyl-sulfonyl)-4-hydroxy-2(1H)-quinolone can be prepared by oxidation of N-(benzylthio)acetyl-4-chloro-anthranilic acid methyl ester with m-chloroperbenzoic acid in dichloromethane and by cyclisation of the N-(benzylsulfonyl)acetyl-4-chloroanthranilic acid methyl ester so obtainable.

EXAMPLE 20

In a manner analogous to that described in Example 7 it is possible by cyclisation of N-(methoxycarbonylmethanesulfonyl)acetyl-4-chloro-anthranilic acid methyl ester to prepare 7-chloro-3-(methoxycarbonylmethanesufonyl)-4-hydroxy-2(1H)-quinolone and to obtain therefrom by hydrolysis by means of sodium hydroxide solution 7-chloro-3-(carboxymethanesulfonyl)-4-hydroxy-2(1H)-quinolone.

The starting material is obtained, for example, by oxidation of N-(methoxycarbonylmethyl-thio)acetyl-4-chloro-anthranilic acid methyl ester with m-chloroperbenzoic acid in dichloro-methane.

EXAMPLE 21

In a manner analogous to that described in Example 1,5,7-dichloro-3-[3-(4-methoxyphenyl)propylthio)-4-hydroxy-2(1H)-quinolone can be prepared by cyclisation of 4,6-dichloro-N-[3-(4-methoxyphenyl)propylthio)acetyl-anthranilic acid methyl ester.

EXAMPLE 22

In a manner analogous to that described in Example 14, 5,7-dichloro-3-[3-(2-fluorophenyl)propylthio)-4-hydroxy-2(1H)-quinolone can be prepared by cyclisation of 4,6-dichloro-N-[3-(2-fluorophenyl)propylthio)acetyl-anthranilic acid methyl ester.

EXAMPLE 23 in a manner analogous to that described in Example 1,5,7-dichloro-3-(benzyl-thio)-4-hydroxy-2(1H)-quinolone can be prepared by cyclisation of 4,6-dichloro-N-(benzyl-thio)acetyl-4-chloro-anthranilic acid methyl ester.

EXAMPLE 24

In a manner analogous to that described in Example 14, 5,7-dichloro-3-[3-(4-fluorophenyl)propylthio)-4-hydroxy-2 (1H)-quinolone can be prepared by cyclisation of 4,6-dichloro-N-[3-(4-fluorophenyl)propylthio)acetyl-anthranilic acid methyl ester.

EXAMPLE 25

0.55 g (1.3 mmol) of 4-chloro-6-nitro-N-(3-phenylpropylthio)acetyl-anthranilic acid methyl ester are placed in 6 ml of tetrahydrofuran at 0° under nitrogen. 2.6 ml of a 1-molar tetrahydrofuran solution of sodium bis-trimethylsilylamide are added dropwise thereto. The mixture is then stirred for 1 hour at 0°. The reaction mixture is poured into 50 ml of 2N hydrochloric acid/ice and extracted with ethyl acetate. The organic phase is dried over sodium sulfate, filtered and concentrated by evaporation. The residue is taken up in a small amount of ethyl acetate, and hexane is added until precipitation begins. The precipitate formed is filtered off with suction and dried. 374 mg (73% of theory) of 7-chloro-5-nitro-4-hydroxy-3-(3-phenylpropylthio)-2(1H)-quinolone are obtained in the form of red crystals having a melting point of 177°–184°.

The starting material can be prepared as follows:

14.2 g (82.3 mmol) of 3-chloro-5-nitro-aniline am dissolved under nitrogen at –65° in 235 ml of dichloromethane, and a solution of 9.8 ml (82.3 mmol) of tert-butyl hypochlorite in 30 ml of dichloromethane is added dropwise thereto. The mixture is then stirred for 10 minutes at –65° and then a solution of 10.6 ml (82.3 mmol) of methylthioacetic acid ethyl ester in 30 ml of dichloromethane is added dropwise thereto. The mixture is stirred for a further 1 hour at –65° and then a solution of 11.5 ml (82.3 mmol) of triethylamine is added dropwise thereto. The mixture is allowed to rise to room temperature, then washed with a small amount of water, dried over sodium sulfate, filtered and concentrated by evaporation. The evaporation residue is taken up in 250 ml of diethyl ether; 30 ml of 2N hydrochloric acid are added and the mixture is stirred at room temperature for 16 hours. The red precipitate is filtered off, washed with diethyl ether and dried. 8.48 g (40% of theon. 1) of 6-chloro-3-methylthio-4-nitro-quinolin-2-one having a melting point of 213° (decorap.) are obtained.

8 g (31 mmol) of 6-chloro-3-methylthio-4-nitroquinolin-2-one and 15.8 g (93 mmol) of copper(II) chloride dihydrate are heated at reflux in 215 ml of acetone and 24 ml of water for 1.5 hours with stirring. The mixture is poured into 600 ml of toluene, filtered, washed with a small amount of water, then dried over sodium sulfate, filtered and concentrated to dryness by evaporation. The residue is made into a suspension with a small amount of ethyl acetate and stirred for 20 minutes; hexane is added until precipitation begins, followed by filtration with suction and drying. 4.28 g (60.9% of theory) of 6-chloro-4-nitro-indoline-2,3-dione are obtained in the form of yellow crystals having a melting point of 227°–231°.

4 ml of a 30% hydrogen peroxide solution are added dropwise at room temperature to 3.8 g (16.7 mmol) of 6-chloro-4-nitro-indoline-2,3-dione in 60 ml of sodium hydroxide solution. The mixture is stirred for 2 hours at room temperature, acidified to pH 2 to 3 with 4N hydrochloric acid, filtered and dried. 3.18 g (87.8% of theory) of 4-chloro-6-nitro-anthranilic acid having a melting point of 202°–205° are obtained.

3.25 g (15 mmol) of 4-chloro-6-nitro-anthranilic acid and 9.73 ml of a 40% aqueous solution of tetrabutylammonium hydroxide are placed in 65 ml of dichloromethane. Then 1.43 ml (15 mmol) of dimethyl sulfate are added dropwise thereto and the mixture is stirred for 1 hour at room temperature and washed in succession with a small amount of water and saturated sodium chloride solution. The aqueous phases are extracted by shaking with dichloromethane and the combined organic phases are dried over sodium sulfate, filtered and concentrated. The residue is stirred with a small amount of ethyl acetate. The product is precipitated with hexane and dried. 1.67 g (48.3% of theory) of 4-chloro-6-nitro-anthranilic acid methyl ester having a melting point of 114°–116° are obtained.

0.3 ml (3.4 mmol) of oxalyl chloride is added under nitrogen to 603 mg (2.87 mmol) of 3-phenylpropylthioacetic acid in 6 ml of dichloromethane and the mixture is stirred under reflux for 2 hours and then concentrated. The residue is taken up in 3 ml of 1,2-dichloro-ethane and added dropwise to a solution of 550 mg (2.39 mmol) of 4-chloro-6-nitro-anthranilic acid methyl ester in 6 ml of 1,2-dichloroethane. The mixture is then stirred for 2 hours at 60°, cooled to room temperature and concentrated by evaporation under reduced pressure. Chromatography on silica gel with hexane/ethylacetate (4:1) as eluant yields 0.57 g (56.4% of theory) of 4-chloro-6-nitro-N-(3-phenylpropylthio)acetyl-anthranilic acid methyl ester in the form of a yellow oil.

EXAMPLE 26

2.2 g (5.31 mmol) of 4,6-dichloro-N-[3-(pyrimidin-5-yl)-propylthio]acetyl-anthranilic acid methyl ester are placed in 25 ml of tetrahydrofuran at 0° under nitrogen. 10.62 ml of a 1-molar tetrahydrofuran solution of sodium bis-trimethylsilylamide are added dropwise thereto. The mixture is then stirred for 2 hours at 0°. The reaction mixture is poured into 50 ml of 2N hydrochloric acid/ice and filtered. The residue is taken up in a small amount of ethyl acetate, and hexane is added until precipitation begins. The precipitate formed is filtered off with suction, washed with hexane and dried. 1.75 g (86.2% of theory) of 5,7-dichloro-4-hydroxy-3-[3-(pyrimidin-5-yl)propylthio)-2-(1H)-quinolone are obtained in the form of red crystals having a melting point of 252°–254°.

The starting material can be prepared as follows:

20 g (0.174 mol) of 5-bromopyrimidine, 19.8 ml (0.35 mol, of propargyl alcohol, 1.22 g (1.74 mol) of bis-triphenylphosphine palladium(II) chloride, 31.3 ml (0.225 mol) of triethyl-amine and 1.62 g (8.5 mmol) of copper(I) chloride are heated at reflux in 160 ml of aceto-nitride for 1 hour, with stirring. The mixture is allowed to cool to room temperature and the acetonitrile is removed under reduced pressure. The residue is taken up in ethyl acetate and washed in succession with water and saturated sodium chloride solution. The aqueous phases are combined and extracted with ethyl acetate. TI-e combined organic phases are dried over sodium sulfate, filtered and concentrated. Chromatography on silica gel with hexane/ethyl acetate (4:1) as eluant yields 5.85 g (25.1% of theory) of 3-(pyrimidin-5-yl)-propargyl alcohol having a melting point of 85°.

5.8 g (43.2 mmol) of 3-(pyrimidin-5-yl)propargyl alcohol at9 hydrogenated with 0.58 g of 5% palladium-on-carbon in 60 ml of tetrahydrofuran at room temperature and normal pressure for 30 hours. The reaction mixture is filtered with suction over a glass fibre filter and concentrated. 4.12 g (69% of theory) of 3-(pyrimidin-5-yl)propanol are obtained in the form of a colourless oil.

9.87 g (51.7 mmol) of tosyl chloride in 50 ml of dichloromethane are added dropwise at room temperature to a solution of 6.5 g (47 mmol) of 3-(pyrimidin-5-yl)propanol and 9 ml (64.6 mmol) of triethylamine in 100 ml dichloromethane that is being stirred under nitrogen. The mixture is stirred for 16 hours at room temperature, then washed with water and saturated sodium chloride solution, dried over sodium sulfate, filtered and concentrated by evaporation under reduced pressure. 14.42 g of 3-(pyrimidin-5-yl)propyl tosylate are obtained, which can be processed further without further purification.

2.36 g (54 mmol) of a 55% suspension of sodium hydride in mineral oil are placed at 0° in 100 ml of tetrahydrofuran. There are then added dropwise at from 0° to 10°, first 4.93 g (45 mmol) of thioglycolic acid ethyl ester and after 20 minutes at 0° a solution of 14.4 g (47 mmol) of 3-(pyrimidin-5-yl)propyl rosylate in 50 ml of terahydrofuran. The mixture is stirred at reflux for 20 minutes, cooled to room temperature, taken up in ethyl acetate, washed with water and saturated sodium chloride solution, dried over sodium sulfate, filtered until clear and concentrated under reduced pressure. Chromatography on silica gel with hexane/ethyl acetate yields 7.82 g (69.2% of theory) of 3-(pyrimidin-5-yl)propylthio-acetic acid ethyl ester in the form of a brown oil.

20 ml (40 mmol) of 2N sodium hydroxide solution are added dropwise to 7.8 g (32.5 mmol) of 3-(pyrimidin-5-yl) propylthioacetic acid ethyl ester in 20 ml of methanol. The mixture is then stirred for 16 hours at room temperature; a small amount of water is added and the mixture is extracted with dichloromethane, dried over sodium sulfate and filtered with suction and the filtrate is concentrated. 3.13 g (46% of theory) of 3-(pyrimidin-5-yl)propyl-thioacetic acid are obtained in the form of a brown oil.

1.83 ml (14.1 mmol) of chloroformic acid butyl ester are added dropwise at 0° under nitrogen to a solution of 3 g (14.1 mmol) of (pyrimidin-5-yl)propylthioacetic acid and 1.55 ml (14.1 mmol) of 4-methylmorpholine in 100 ml of dichloromethane. The mixture is stirred for 40 minutes at 0°; 3.1 g (14.1 mmol) of 4,6-dichloranthranilic acid methyl ester are added and the mixture is then stirred for 20 hours. The reaction mixture is washed with a small amount of water and saturated sodium chloride solution, dried over sodium sulfate and concentrated by evaporation. Chromatography on silica gel with hexane/ethyl acetate (2:1) as eluant yields 2.39 g (40.9% of theory) of 4,6-dichloro-N-[3-(pyrimidin-5-yl)propylthio]acetyl-anthranilic acid methyl ester in the form of a yellow oil.

EXAMPLE 27

1.88 g (4.5 mmol) of 4,6-dichloro-N-[3-(2-thienyl) propylthioacetyl]-anthranilic acid methyl ester are dissolved under argon in 25 ml of tertrahydrofuran; a total of 13.5 ml (13.5 mmol) of a 1-molar solution of sodium bis-trimethylsilylamide in tetrahydrofuran is added in portions at from 0° to 5° and the mixture is then stirred for 3 hours at room temperature. The light-brown solution is poured onto a mixture of 40 ml of 2N hydrochloric acid and ice-water, stirred thoroughly, filtered with suction and washed neutral with ice-water. The filtration residue is dried under reduced pressure for 1 hour at 40°, dissolved in 100 ml of ethyl acetate, and 100 ml of hexane are added. The precipitate formed is filtered off with suction, washed with a small amount of hexane and dried at 40° under reduced pressure. After recrystallisation from ethanol, 1.36 g (78.2% of theory) of 5,7-dichloro-3-[3-(2-thienyl)-propylthio)-4-hydroxy-2(1H)-quinolone, melting point 205°–207°, are obtained.

The starting material can be prepared, for example, as follows:

Esterification of 7.7 g (20 mmol) of 3-(2-thienyl)acrylic acid with 50 ml of ethanol in the presence of 2 ml of concentrated sulfuric acid yields 8.75 g (96% of theory) of 3-(2-thienyl)-acrylic acid ethyl ester in the form of a light-brown oil.

Hydrogenation of 1.82 g (10 mmol) of 3-(2-thienyl) acrylic acid ethyl ester in 40 ml of ethanol under normal pressure and in the presence of 0.9 g of 5% palladium-on-carbon yields 1.71 g (92.8% of theory) of 3-(2-thienyl) propionic acid ethyl ester in the form of a colourless oil.

Reduction of 8.3 g (45 mmol) of 3-(2-thienyl)prepionic acid ethyl ester with 2.56 g (67.5 mmol) of lithium aluminium hydride in 150 ml of tetrahydrofuran yields 6.25 g (97.6% of theory) of 3-(2-thienyl)propanol in the form of a colourless liquid.

Bromination of 6.2 g (43.6 mmol) of 3-(2-thienyl) propanol with 9 ml (96 mmol) of phosphorus tribromide in 80 ml of tetrachloromethane yields 3.95 g (44.17% of theory) of 3-(2-thienyl)propyl bromide in the form of a bright-yellow liquid.

995 mg (22.8 mmol) of sodium hydride in the form of a 55% suspension in mineral oil are placed at from 0° to 5° in 30 ml of tetrahydrofuran, and 2.1 25 ml (19 mmol) of thioglycolic acid ethyl ester are added dropwise thereto. The mixture is stirred for 30 minutes at from 0° to 5°; 3.9 g (19 mmol) of 3-(2-thienyl)propyl bromide are added dropwise under nitrogen at from 0° to 5° and the mixture is allowed to rise to room temperature and is then stirred for 3 hours. The mixture is then again cooled to from 0° to 5°, 200 ml of ethyl acetate and 100 ml of ice-water are added and the organic phase is separated off and then shaken twice with 100 ml of ethyl acetate each time. The combined organic phases are washed three times with 100 ml of water each time and then with saturated sodium chloride solution, dried over sodium sulfate, filtered, concentrated by evaporation under reduced pressure at 35° and distilled. 3.755 g (80.2% of theory) of 3-(2-thienyl)propylthioacetic acid ethyl ester are obtained in the form of a bright-yellow liquid.

Hydrolysis of 3.745 g (15.3 mmol) of 3-(2-thienyl) propylthioacetic acid ethyl ester with 10 ml of 2N sodium hydroxide solution in 30 ml of ethanol yields 3.26 g (98.5% of theory) of 3-(2-thienyl)-propylthioacetic acid ethyl ester in the form of a blight-yellow oil; chlorination of 3.24 g (15 mmol) thereof with 2.84 ml (33 mmol) of oxalyl chloride in 35 ml of dichloromethane yields 3-(2-thienyl) propylthioacetyl chloride in the; form of a yellow oil and reaction thereof for 16 hours with 2.97 g (13.5 mmol) of 4,6-dichloroanthranilic acid methyl ester in the presence of 2.3 ml (16.5 mmol) of triethylamine in 80 ml of dichloromethane at room temperature, dilution with 200 ml of dichloromethane, washing with water (3×100 ml) and 100 ml of saturated sodium chloride solution, drying over sodium sulfate, concentration by evaporation under reduced pressure and chromatography on silica gel with toluene as eluant yield 1.97 g (34.9% of the theoretical total yield) of 4,6-dichloro-N-[3-(2-thienyl)-propylthioacetyl]-anthranilic acid methyl ester in the form of a yellowish oil.

EXAMPLE 28

In a manner analogous to that described in Example 27, 5,7-dichloro-3-[3-(3-thienyl)propylthio)-4-hydroxy-2(1H)-quinolone, melting point 194°–196°, is obtained starting from 3-(3-thienyl)acrylic acid and via 4,6-dichloro-N-[3-(3-thienyl)propylthioacetyl]-anthranilic acid methyl ester.

EXAMPLE 29

In a manner analogous to that described in Example 14, 7-chloro-3-benzyloxy-4-hydroxy-2(1H)-quinolone, melting point 223°–226°, is obtained by cyclisation of 6-chloro-N-(benzyloxyacetyl)-anthranilic acid methyl ester by means of sodium N,N-bis(trimethylsilyl)-amide in tetrahydrofuran.

EXAMPLE 30

In a manner analogous to that described in Example 27, 5,7-dichloro-3-(1,2,3,4-tetrahydronaphth-2-ylmethylthio)-4-hydroxy-2(1H)-quinolone, melting point 213°–215°, is obtained starting from 1,2,3,4-tetrahydronaphthoic acid and via 4,6-dichloro-N-(1,2,3,4-tetrahydronaphth-2-ylmethylthioacetyl)-anthranilic acid methyl ester.

EXAMPLE 31

In a manner analogous to that described in Example 27, 5,7-dichloro-3-(1,4-benzodioxan-2-ylmethylthio)-4-hydroxy-2(1H)-quinolone, melting point 252°–254°, is obtained starting from 1,4-benzodioxan-2-ylmethanol and via 4,6-dichloro-N-(1,4-benzodioxan-2-yl-methylthioacetyl)-anthranilic acid methyl ester.

EXAMPLE 32

In a manner analogous to that described in Example 27, 5,7-dichloro-3-(chroman-3-ylmethylthio)-4-hydroxy-2(1H)-quinolone, melting point 256°–258°, is obtained starting from chroman-3-carboxylic acid and via 4,6-dichloro-N-(chroman-3-ylmethylthio-acetyl)-anthranilic acid methyl ester.

EXAMPLE 33

In a manner analogous to that described in Example 1, 5,7-dichloro-3-(2-phenyloxyethylthio)-4-hydroxy-2(1H)-quinolone, melting point 229°–231°, is obtained by cyclisation of 4,6-dichloro-N-(2-phenyloxyethylthioacetyl)-anthranilic acid methyl ester by means of sodium N,N-bis(trimethylsilyl)amide in tetrahydrofuran.

EXAMPLE 34

In a manner analogous to that described in Examples 1,7 to 9 and 11 to 15 it is also possible to prepare:

5,7-dichloro-3-(3-phenylpropylthio)-4-hydroxy-2(1H)-quinolone, melting point 205°–206°;

7-chloro-3-heptylthio-4-hydroxy-2(1H)-quinolone, melting point 155°–157°;

7-chloro-3-ylthio-4-hydroxy-2(1H)-quinolone, melting point 296°;

7-chloro-3-ethoxycarbonylmethylthio-4-hydroxy-2(1H)-quinolone, melting point 194°–197°;

7-chloro-3-(N-methylcarbamoylmethylthio)-4-hydroxy-2(1H)-quinolone, melting point 253°–255°;

7-chloro-3-(3-trans-phenylprop-2-enylthio)-4-hydroxy-2(1H)-quinolone, melting point 209°–211°;

7-chloro-3-(3-cis-phenylprop-2-enylthio)-4-hydroxy-2(1H)-quinolone;

3-carboxymethyl-5,7-dichloro-4-hydroxy-2(1H)-quinolone, melting point above 300°;

3-benzylthio-4-hydroxy-2(1H)-quinolone;

4-hydroxy-3-(2-phenylethylthio)-2(1H)-quinolone;

4-hydroxy-3-(3-phenylpropylthio)-2(1H)-quinolone;

4-hydroxy-3-(4-phenylbutylthio)-2(1H)-quinolone;

3-(carboxymethylthio)-4-hydroxy-2(1H)-quinolone;

3-(3-carboxypropylthio)-4-hydroxy-2(1H)-quinolone;

4-hydroxy-3-(3-methoxycarbonylpropylthio)-2(1H)-quinolone.

EXAMPLE 35

Tablets, each comprising 50 mg of 3-(3-carboxypropylthio)-2(1H)-quinolone or a salt, for example the sodium salt, thereof can be prepared as follows:

| Composition (10000 tablets) | |
|---|---|
| active ingredient | 500.0 g |
| lactose | 500.0 g |
| potato starch | 352.0 g |
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 g of the potato starch and the mixture is moistened with an ethanolic solution of the gelatin and granulated through a sieve. After drying, the remainder of the potato starch, the, magnesium stearate, the talc and the silicon dioxide are mixed in and the mixture is compressed to form tablets each weighing 145.0 mg and comprising 50.0 mg of active ingredient; if desired, the tablets may be provided with dividing notches for finer adaptation of the close.

EXAMPLE 36

A sterile-filtered aqueous gelatin solution comprising 20% cyclodextrins as solubiliser and 3 mg of 3-(3-carboxypropylthio)-2(1H)-quinolone or of a salt, for example the sodium salt, thereof as active ingredient is so mixed with heating under aseptic conditions with a sterile gelatin solution containing phenol as preservative that 1.0 ml of solution has the following composition:

| | |
|---|---|
| active ingredient | 3 mg |
| gelatin | 150.0 mg |
| phenol | 4.7 mg |
| dist. water containing 20% cyclodextrins as solubiliser | 1.0 ml |

EXAMPLE 37

For the preparation of a sterile dry substance for injection comprising 5 mg of 3-(3-carboxypropylthio)-2(1H)-quinolone or of a salt, for example the sodium salt, thereof, 5 mg of one of the compounds of formula I mentioned in the preceding Examples is dissolved as active ingredient in 1 ml of an aqueous solution containing 20 mg of mannitol and 20% cyclodextrins as solubiliser. The solution is sterile-filtered and under aseptic conditions introduced into a 2 ml ampoule, deep-frozen and lyophilised. Before use, the lyophilisate is dissolved in 1 ml of distilled water or 1 ml of physiological saline solution. The solution is administered intramuscularly or intravenously. This formulation can also be introduced into double-chamber disposable syringes.

EXAMPLE 38

For the preparation of 10 000 film-coated tablets, each comprising 100 mg of 3-(3-carboxypropylthio)-2(1H)-quinolone or of a salt, for example the sodium salt, thereof, the method of preparation is as follows:

| | |
|---|---|
| active ingredient | 1000 g |
| corn starch | 680 g |
| colloidal silicic acid | 200 g |
| magnesium stearate | 20 g |
| stearic acid | 50 g |
| sodium carboxymethyl starch | 250 g |
| water | q.s. |

A mixture of one of the compounds of formula I mentioned in the preceding Examples, as active ingredient, 50 g of corn starch and the colloidal silicic acid is processed to form a moist mass with a starch paste consisting of 250 g of corn starch and 2.2 kg of demineralised water. The mass is forced through a sieve of 3 mm mesh size and added in a fluidised-bed drier at 45° for 30 minutes. The dried granules are then pressed through a sieve of 1 mm mesh size, mixed with a previously sieved mixture (I mm sieve) of 330 g of corn starch, the magnesium stearate, the stearic acid and the sodium carboxymethyl starch and compressed to form slightly biconvex tablets.

EXAMPLE 39

In a manner analogous to that described in Examples 35 to 38 it is also possible to prepare pharmaceutical compositions comprising a different compound according to any one of Examples 1 to 34.

What is claimed is:

1. A compound of formula I:

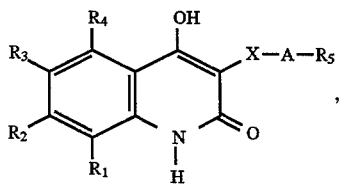

wherein $R_1$ and $R_3$ are hydrogen,
$R_2$ is halogen having an atomic number of up to and including 35,
$R_4$ is hydrogen, halogen having an atomic number of up to and including 35, $C_1$–$C_4$alkyl or nitro,
X is thio,
A is straight-chain $C_1$–$C_4$alkylene, and
$R_5$ is phenyl, pyrimidinyl, chromanyl, 1,4-benzodioxanyl, thienyl or 1,2,3,4-tetrahydronaphth-2-yl each of which is unsubstituted or mono- or di-substituted by one or more of halogen having an atomic number of up to and including 35, cyano, carboxy, $C_1$–$C_4$alkoxycarbonyl, N-$C_1$–$C_4$alkylcarbamoyl, N-phenyl-N-$C_1$–$C_4$alkylcarbamoyl, hydroxy, $C_1$–$C_4$alkanoyl and $C_1$–$C_4$alkyl; carboxy, $C_1$–$C_4$alkoxycarbonyl or N-$C_1$–$C_4$alkylcarbamoyl, or a tautomer or salt thereof.

2. A compound according to claim 1 wherein
$R_5$ is phenyl that is unsubstituted or substituted by one or more of halogen having an atomic number of up to and including 35, $C_1$–$C_4$alkoxy and carboxy; thienyl, 1,2,3,4-tetrahydronaphth-2-yl, pyrimidin-5-yl, chroman-2-yl, 1,4-benzodioxan-3-yl, carboxy or $C_1$–$C_4$alkoxycarbonyl,
or a tautomer or salt thereof.

3. A compound according to claim 1 wherein
$R_4$ is hydrogen, $C_1$–$C_4$alkyl or halogen having an atomic number of up to and including 35, and
$R_5$ is phenyl that is unsubstituted or substituted by halogen having an atomic number of up to and including 35; carboxy or $C_1$–$C_4$alkoxycarbonyl,
or a tautomer or salt thereof.

4. A pharmaceutical composition comprising a compound according to claim 1 or a pharmaceutically acceptable salt thereof.

5. A method of treating of pathological conditions that are responsive to glycine-antagonistic blocking of NMDA-sensitive receptors which comprises administering to a warm-blooded animal requiring such treatment a therapeutically effective amount of a compound according to claim 1 or of a pharmaceutically acceptable salt thereof.

6. A compound as claimed in claim 1, said compound being selected from the group consisting of:

7-Chloro-4-hydroxy-3-(3-phenylpropylthio)-2(1H)-quinolone;
7-Chloro-5-ethyl-4-hydroxy-3-(3-phenylpropylthio)-2(1H)-quinolone;
7-Chloro-4-hydroxy-3-(2-phenethylthio)-2(1H)-quinolone;
7-Chloro-5-(hex-1-enyl)-4-hydroxy-3-(3-phenylpropylthio)-2(1H)-quinolone;
5,7-Dichloro-4-hydroxy-3-[3-(4-methoxycarbonylphenyl)propylthio]-2(1H)-quinolone;
5,7-Dichloro-4-hydroxy-3-[3-(4-carboxyphenyl)propylthio]-2(1H)-quinolone;
5,7-Dichloro-4-hydroxy-3-[3-(3-methoxycarbonylphenyl)propylthio]-2(1H)-quinolone;
5,7-Dichloro-4-hydroxy-3-[3-(3-carboxyphenyl)propylthio]-2(1H)-quinolone;
7-Chloro-4-hydroxy-3-(methoxycarbonylmethylthio)-2(1H)-quinolone;
7-Chloro-4-hydroxy-3-(carboxymethylthio)-2(1H)-quinolone;
5,7-Dichloro-4-hydroxy-3-(carboxymethylthio)-2(1H)-quinolone;
7-Chloro-4-hydroxy-3-(3-methoxycarbonylpropylthio)-2(1H)-quinolone;
3-(3-Carboxypropylthio)-7-chloro-4-hydroxy-2(1H)-quinoline;
7-Chloro-3-(4-phenylbutylthio)-4-hydroxy-2(1H)-quinolone:
7-Chloro-3-(benzylthio)-4-hydroxy-2(1H)-quinolone;
7-Chloro-4-hydroxy-3-(1-carboxy-3-phenyl-propylthio)-2(1H)-quinolone;
7-Chloro-4-hydroxy-3-(2-hydroxy-3-phenyl-propylthio)-2(1H)-quinolone;
7-Chloro-4-hydroxy-3-(2-hydroxyethylthio)-2(1H)-quinolone;
5,7-Dichloro-3-[3-(4-methoxyphenyl)propylthio]-4-hydroxy-2(1H)-quinolone;
5,7-Dichloro-3-[3-(2-fluorophenyl)propylthio]-4-hydroxy-2(1H)-quinolone;
5,7-Dichloro-3-(benzylthio)-4-hydroxy-2(1H)-quinolone;
5,7-Dichloro-3-[3-(4-fluorophenyl)propylthio]-4-hydroxy-2(1H)-quinolone;
7-Chloro-5-nitro-4-hydroxy-3-(3-phenylpropylthio)-2(1H)-quinolone;
5,7-Dichloro-4-hydroxy-3-[3-(pyrimidin-5-yl)propylthio]-2(1H)-quinolone;
5,7-Dichloro-3-[3-(2-thienyl)propylthio]-4-hydroxy-2(1H)-quinolone;
5,7-Dichloro-3-[3-(thien-3-yl)propylthio]-4-hydroxy-2(1H)-quinolone;
7-Chloro-3-benzyloxy-4-hydroxy-2(1H)-quinolone;
5,7-Dichloro-3-(1,2,3,4-tetrahydronaphth-2-ylmethylthio)-4-hydroxy-2(1H)-quinolone;
5,7-Dichloro-3-(1,4-benzodioxan-2-ylmethylthio)-4-hydroxy-2(1H)-quinolone;
5,7-Dichloro-3-(chroman-3-ylmethylthio)-4-hydroxy-2(1H)-quinolone;
5,7-Dichloro-3-(2-phenyloxyethylthio)-4-hydroxy-2(1H)-quinolone; and
5,7-Dichloro-3-(3-phenylpropylthio)-4-hydroxy-2(1H)-quinolone,
or a salt thereof.

* * * * *